(12) United States Patent
Hirschmann et al.

(10) Patent No.: US 6,821,582 B2
(45) Date of Patent: Nov. 23, 2004

(54) LIQUID-CRYSTALLINE MIXTURES

(75) Inventors: Harald Hirschmann, Darmstadt (DE);
Volker Reiffenrath, Rossdorf (DE);
Marcus Reuter, Darmstadt (DE);
Sabine Schoen, Herten-Westerholt (DE); Sven Schüpfer, Aschaffenburg (DE); Clarissa Weller, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/205,491

(22) Filed: Jul. 26, 2002

(65) Prior Publication Data
US 2003/0127629 A1 Jul. 10, 2003

(30) Foreign Application Priority Data
Jul. 27, 2001 (DE) .......................................... 101 36 750

(51) Int. Cl.[7] .................... C09K 19/30; C09K 19/34; C09K 19/12; C09K 19/20; G02F 1/133
(52) U.S. Cl. .............. 428/1.1; 252/299.61; 252/299.63; 252/299.66; 252/299.67
(58) Field of Search .................. 252/299.63, 299.61, 252/299.66; 428/1.1

(56) References Cited

U.S. PATENT DOCUMENTS 5,997,767 A * 12/1999 Hirschmann et al. .. 252/299.63
6,017,467 A * 1/2000 Fujita et al. ........... 252/299.01
6,444,279 B1 * 9/2002 Reiffenrath et al. .......... 428/1.1

FOREIGN PATENT DOCUMENTS

DE 10058474 * 7/2001

* cited by examiner

*Primary Examiner*—Shean C. Wu
(74) *Attorney, Agent, or Firm*—Millen, White, Zelano & Branigan, P.C.

(57) ABSTRACT

A liquid-crystalline mixture that contains one or more compounds of each of the formulae IA, IB and IC

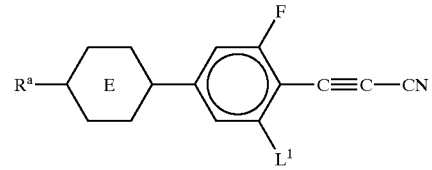

IA

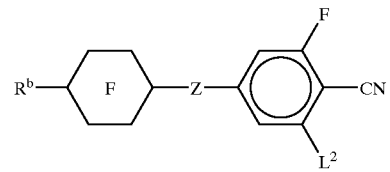

IB

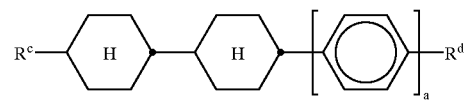

IC and to the use thereof in TN, STN and IPS displays.

33 Claims, No Drawings

LIQUID-CRYSTALLINE MIXTURES

One aspect of the invention relates to liquid-crystalline mixtures for twisted nematic (TN) and supertwisted nematic (STN) liquid-crystal displays having very short response times and good steepnesses and angle dependencies. The mixtures according to the invention are furthermore also suitable for IPS (in plane switching) displays.

TN displays are known, for example from M. Schadt and W. Helfrich, Appl. Phys. Lett., 18, 127 (1971). STN displays are known, for example from EP 0 131 216 B1; DE 34 23 993 A1; EP 0 098 070 A2; M. Schadt and F. Leenhouts, 17th Freiburg Congress on Liquid Crystals (8.-10.04.87); K. Kawasaki et al., SID 87 Digest 391 (20.6); M. Schadt and F. Leenhouts, SID 87 Digest 372 (20.1); K. Katoh et al., Japanese Journal of Applied Physics, Vol. 26, No. 11, L 1784–L 1786 (1987); F. Leenhouts et al., Appl. Phys. Lett. 50 (21), 1468 (1987); H. A. van Sprang and H. G. Koopman, J. Appl. Phys. 62 (5), 1734 (1987); T. J. Scheffer and J. Nehring, Appl. Phys. Lett. 45 (10), 1021 (1984), M. Schadt and F. Leenhouts, Appl. Phys. Lett. 50 (5), 236 (1987) and E. P. Raynes, Mol. Cryst. Liq. Cryst. Letters Vol. 4 (1), pp. 1–8 (1986). The term STN here covers any relatively highly twisted display element having a twist angle with a value of between 160° and 360°, such as, for example, the display elements according to Waters et al. (C. M. Waters et al., Proc. Soc. Inf. Disp. (New York) (1985) (3rd Intern. Display Conference, Kobe, Japan), STN-LCDs (DE-A 35 03 259), SBE-LCDs (T. J. Scheffer and J. Nehring, Appl. Phys. Lett. 45 (1984) 1021), OMI-LCDs (M. Schadt and F. Leenhouts, Appl. Phys. Lett. 50 (1987), 236, DST-LCDs (EP-A 0 246 842) or BW-STN-LCDs (K. Kawasaki et al., SID 87 Digest 391 (20.6)).

STN displays are distinguished from standard TN displays by significantly better steepnesses of the electro-optical characteristic line and, at moderate and relatively high multiplex rates, for example from 32 to 64, by better contrast values. On the other hand, the contrast in TN displays is generally higher, owing to the better dark value, and the angle dependence of the contrast is lower than in STN displays having low multiplex rates of, for example, less than 32.

Of particular interest are TN and STN displays having very short response times, in particular at relatively low temperatures. In order to achieve short response times, the rotational viscosities of the liquid-crystal mixtures have hitherto been optimised using mostly monotropic additives having relatively high vapor pressure. However, the response times achieved were not adequate for every application.

In order to achieve a steep electro-optical characteristic line in the displays according to the invention, the liquid-crystal mixtures should have relatively large values for the ratio between the elastic constants $K_{33}/K_{11}$ and relatively small values for $\Delta\epsilon/\epsilon_\perp$, where $\Delta\epsilon$ is the dielectric anisotropy and $\epsilon_\perp$ is the dielectric constant perpendicular to the longitudinal molecular axis.

In addition to optimisation of the contrast and response times, further important requirements are made of mixtures of this type:

1. broad d/p window
2. high long-term chemical stability
3. high electrical resistance
4. low frequency and temperature dependence of the threshold voltage.

The parameter combinations achieved in the art are still far from adequate, in particular for high-multiplex STN displays (with a multiplex rate in the region of about 1/400), but also for medium- and low-multiplex STN displays (with multiplex rates in the region of about 1/64 and 1/16 respectively), and TN displays. This is partly attributable to the fact that the various requirements are affected in opposite manners by material parameters.

Thus, there continues to be a great demand for TN and STN displays, in particular for moderate- and low-multiplex STN displays, having very short response times at the same time as a large working-temperature range, high characteristic-line steepness, good angle dependence of the contrast and low threshold voltage which meet the above-mentioned requirements.

One of the objects of the invention is to provide TN and STN displays which do not have the above-mentioned disadvantages or do so only to a lesser extent, and at the same time have short response times, in particular at low temperatures, and very good steepnesses.

Upon further study of the specification and appended claims, further objects and advantages of this invention will become apparent to those skilled in the art.

These objects can be achieved by using nematic liquid-crystal mixtures which comprise one or more compounds of formula IA,

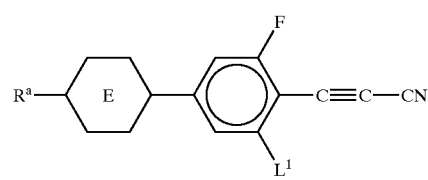

IA one or more compounds of formula IB,

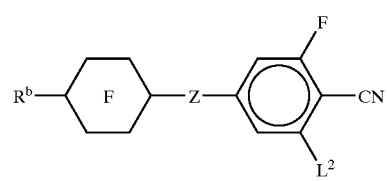

IB and
one or more compounds of formula IC,

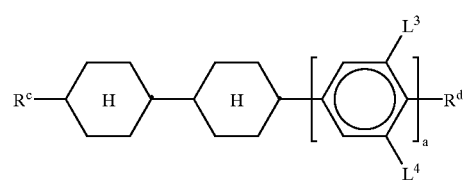

IC wherein
$R^a$, $R^b$ and $R^d$ are each, independently of one another, an alkyl group having up to 12 carbon atoms which is unsubstituted or substituted by at least one halogen atom and in which one or two non-adjacent $CH_2$ groups may be replaced by —O—, —CH=CH—, —CO—, —OCO— or —CO—O— in such a way that O atoms are not linked directly to one another, where, in the case where a=1, $R^d$ may alternatively be F, Cl, OCHFCF$_3$, CF$_3$ or OCF$_3$, $R^c$ is alkenyl or alkenyloxy having from 2 to 6 carbon atoms,

[Structural formula fragments:]

—⬡E— is —⬡H—,

—⬡—, —⬡(F)—, —⬡(F,F)(F)—,

—⬡(O,O)— or —⬡(N,N)—,

—⬡F— is —⬡—,

—⬡(F,F)—, —⬡(F,F)— or

—⬡H—,

Z is —CO—O—, —CF$_2$O—, —OCF$_2$— or a single bond,

L$^1$ to L$^4$ are each, independently of one another, H or F, and a is 0 or 1, where the proportion of compounds of formula IC in the mixture is at least 25% by weight.

The use of the compounds of the formulae IA, IB and IC in the mixtures for TN and STN displays according to the invention results in at least high steepness of the electro-optical characteristic line, low temperature dependence of the threshold voltage, and very fast response times, in particular at low temperatures.

The compounds of the formulae IA, IB and IC significantly shorten, in particular, the response times of TN and STN mixtures while simultaneously increasing the steepness and low temperature dependence of the threshold voltage.

The mixtures according to the invention are furthermore distinguished by at least the following advantages:

they have low viscosity, they have low threshold voltage and operating voltage, and they effect long shelf lives in the LC display at low temperatures.

The mixtures according to the invention are also suitable for IPS displays.

The mixtures according to the invention are, in particular, suitable for liquid-crystal displays having two outer plates, which, together with a frame, form a cell, a nematic liquid-crystal mixture of positive dielectric anisotropy located in the cell, electrode layers with alignment layers on the insides of the outer plates, a tilt angle between the longitudinal axis of the molecules at the surface of the outer plates and the outer plates of from 0 degree to 30 degrees, and a twist angle of the liquid-crystal mixture in the cell from alignment layer to alignment layer with a value of between 22.5° and 600°.

Liquid-crystal displays of this type preferably contain a nematic liquid-crystal mixture comprising a) 15–80% by weight of a liquid-crystalline component A containing one or more compounds having a dielectric anisotropy of greater than +1.5;

b) 25–85% by weight of a liquid-crystalline component B containing one or more compounds having a dielectric anisotropy of between −1.5 and +1.5;

c) 0–20% by weight of a liquid-crystalline component D containing one or more compounds having a dielectric anisotropy of below −1.5, and d) if desired, an optically active component C in such an amount that the ratio between the layer thickness (separation of the outer plates) and the natural pitch of the chiral nematic liquid-crystal mixture is greater than about 0.2, preferably 0.2 to 1.3, characterised in that they comprise at least one compound of formula IA,

IA

R$^a$—⬡E—⬡(F,L$^1$)—C≡C—CN one or more compounds of formula IB,

IB

R$^b$—⬡F—Z—⬡(F,L$^2$)—CN and one or more compounds of formula IC,

IC

R$^c$—⬡H—⬡H—[⬡(L$^3$,L$^4$)]$_a$—R$^d$ wherein

R$^a$, R$^b$ and R$^d$ are each, independently of one another, an alkyl group having up to 12 carbon atoms which is unsubstituted or substituted by at least one halogen atom and in which one or two non-adjacent CH$_2$ groups may be replaced by —O—, —CH=CH—, —CO—, —OCO— or —CO—O— in such a way that O atoms are not linked directly to one another, where, in the case where a=1, R$^d$ may alternatively be F, Cl, OCHFCF$_3$, CF$_3$ or OCF$_3$, R$^c$ is alkenyl or alkenyloxy having from 2 to 6 carbon atoms, -E- is -H-,

[structures: phenyl, fluorophenyl, difluorophenyl]

[structures: dioxane, pyrimidine]

-F- is -⌬-,

[structures: fluorophenyl, difluorophenyl] or

-H-,

Z is —CO—O—, —CF$_2$O—, —OCF$_2$— or a single bond,

L$^1$ to L$^4$ are each, independently of one another, H or F, and a is 0 or 1, where the proportion of compounds of the formula IC in the mixture is at least 25% by weight.

The invention also relates to TN and STN displays, in particular moderate- and low-multiplexed STN displays.

Preference is given to liquid-crystal mixtures which comprise one or more compounds of the formula IA in which R$^a$ is a straight-chain alkyl group having from 1 to 8 carbon atoms or an alkenyl group having 2–8 carbon atoms.

Preference is furthermore given to liquid-crystal mixtures which comprise one or more compounds of formula IB in which R$^b$ is a straight-chain alkyl or alkenyl group having from 1 or 2 to 8 carbon atoms respectively.

The mixtures according to the invention comprise, in particular, one or more, preferably one or two, compounds of the sub-formulae IA-1 to IA-4:

IA-1
[structure: R$^a$-cyclohexyl-fluorophenyl-C≡C-CN with L$^1$]

IA-2
[structure: R$^a$-pyrimidine-fluorophenyl-C≡C-CN with L$^1$]

IA-3
[structure: R$^a$-phenyl-fluorophenyl-C≡C-CN with L$^1$]

IA-4
[structure: R$^a$-dioxane-fluorophenyl-C≡C-CN with L$^1$]

wherein R$^a$ is as defined above.

Preferred compounds of the formula IA-1 are those selected from the group consisting of IA-1 a to IA-1c IA-1a
[structure: alkyl-cyclohexyl-fluorophenyl-C≡C-CN with L$^1$]

IA-1b
[structure: R$^{1a}$-CH=CH-cyclohexyl-fluorophenyl-C≡C-CN with L$^1$]

IA-1c
[structure: R$^{1a}$-alkenyl-cyclohexyl-fluorophenyl-C≡C-CN with L$^1$]

wherein R$^{1a}$ is H, CH$_3$, C$_2$H$_5$ or n—C$_3$H$_7$, and alkyl is an alkyl group having from 1 to 8 carbon atoms.

Preferred compounds of the formula IA-2 are those selected from the group consisting of IA-2a to IA-2c:

IA-2a
[structure: alkyl-pyrimidine-fluorophenyl-C≡C-CN with L$^1$]

IA-2b
[structure: R$^{1a}$-CH=CH-pyrimidine-fluorophenyl-C≡C-CN with L$^1$]

IA-2c

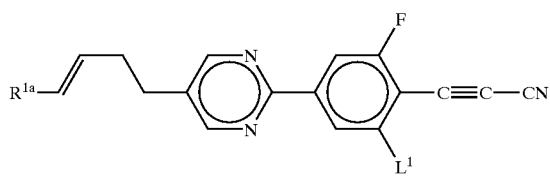

wherein R$^{1a}$ is H, CH$_3$, C$_2$H$_5$ or n—C$_3$H$_7$, and alkyl is an alkyl group having from 1 to 8 carbon atoms.

The mixtures according to the invention preferably comprise one or more compounds of the formulae IA-1a and/or IA-2a.

Further preferred compounds in the mixtures according to the invention are those of the formulae IA-1b, IA-1c, IA-2b and IA-2c in which R$^{1a}$ is H.

The media according to the invention preferably comprise one or more compounds of the formula IA-1 and/or one or more compounds of the formula IA-2, in particular those of the preferred sub-formulae mentioned above.

The medium according to the invention preferably comprises one or more compounds of the formulae selected from the group consisting of IB-1 to IB-7:

IB-1
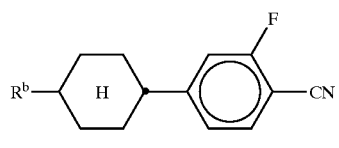

IB-2
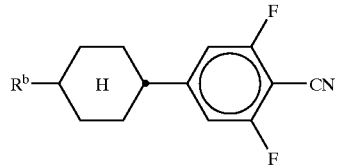

IB-3
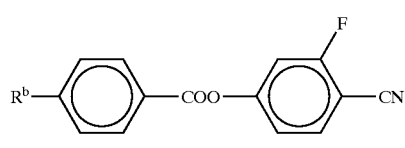

IB-4
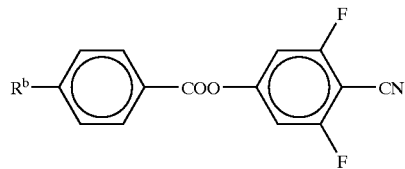

IB-5
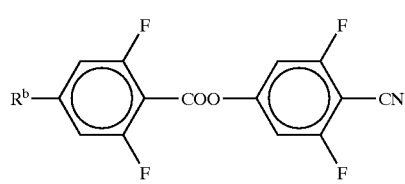

IB-6
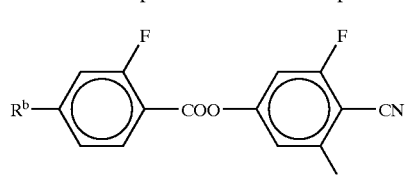

IB-7
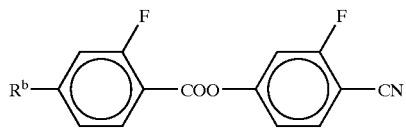

wherein R$^b$ is as defined above.

Of the sub-formulae, preference is given to compounds in which R$^b$ is a straight-chain alkyl radical having 1–8 carbon atoms or a straight-chain alkenyl radical having 2–8 carbon atoms.

The medium according to the invention preferably comprises one, two, three or four, preferably three or four, compounds of the formulae IB-1, IB-2, IB-3 and/or IB-4.

Preferred compounds of formula IB-4 are,

IB-4a
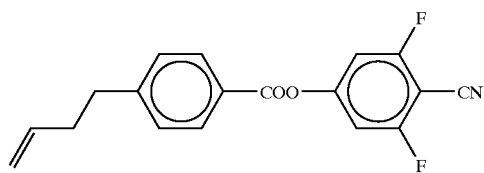

IB-4b
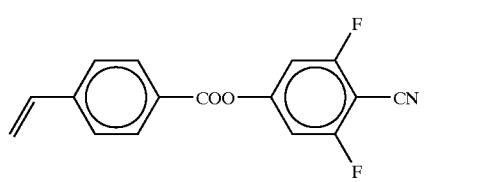

IB-4c
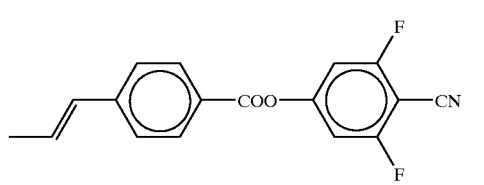

Preferred compounds of the formula IC are those in which R$^c$ is alkenyl having from 2 to 7 carbon atoms, in particular compounds selected from the formulae IC-1a to IC-1e:

IC-1a
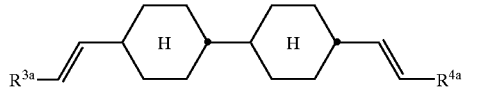

IC-1b
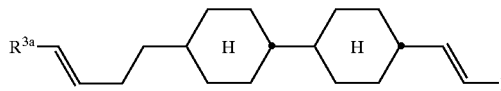

IC-1c
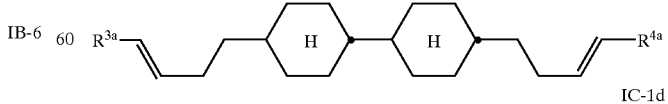

IC-1d
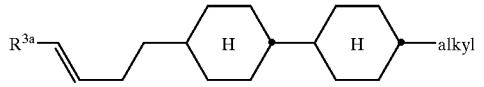

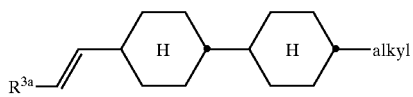

wherein $R^{3a}$ and $R^{4a}$ are each, independently of one another, H, $CH_3$, $C_2H_5$ or n—$C_3H_7$.

Preference is given to compounds of the formula IC-1a, in particular those in which $R^{3a}$ and $R^{4a}$ are $CH_3$, and to compounds of the formula IC-1e in which $R^{3a}$ is H.

Preference is given to TN and STN displays according to the invention in which the liquid-crystal mixture comprises at least one compound of the formulae IC-1a and/or IC-1c in which $R^{3a}$ and $R^{4a}$ each have the same meaning, and to displays in which the liquid-crystal mixture comprises at least one compound of the formula IC-1e.

In a further preferred embodiment, the mixtures according to the invention comprise one or more compounds of the formulae IC-2 and/or IC-3:

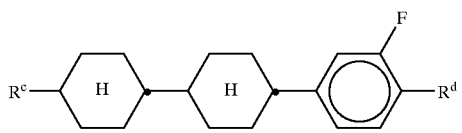

wherein $R^c$ and $R^d$ are as defined above.

Preference is given to compounds of formulae IC-2 and IC-3 wherein $R^d$ is F, $OCF_3$ or alkyl having from 1 to 8, in particular 1, 2 or 3, carbon atoms, and $R^c$ is 1E-alkenyl or 3E-alkenyl having from 2 to 7, in particular 2, 3 or 4, carbon atoms, and to compounds selected from formulae IC-2a to IC-2d and IC-3a:

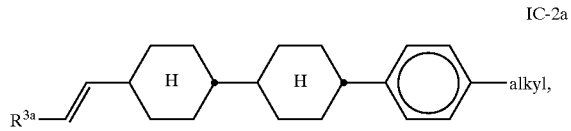

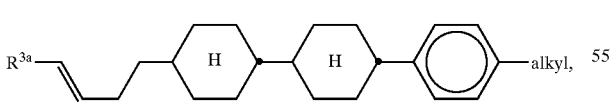

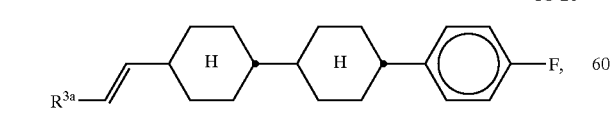

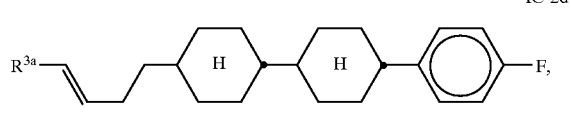

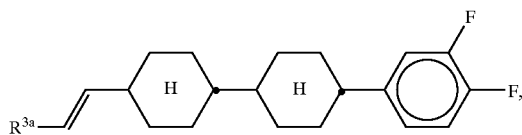

wherein $R^{3a}$ and $R^{4a}$ are each, independently of one another, H, $CH_3$, $C_2H_5$ or n—$C_3H_7$, and alkyl is an alkyl group having from 1 to 8 carbon atoms.

Besides the compounds of the formulae IA, IB and IC, the mixtures according to the invention preferably comprise compounds of the formulae II and/or III

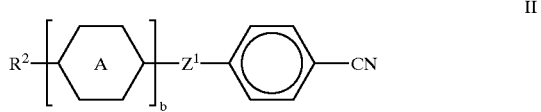

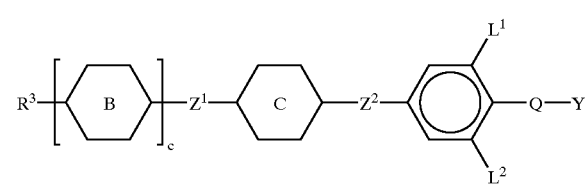

wherein
$R^2$ and $R^3$ are each, independently of one another, an alkyl, alkoxy or alkenyl group having up to 12 carbon atoms, in which, in addition, one or two non-adjacent $CH_2$ groups may be replaced by —O—, —CH=CH—, —CO—, —OCO— or —CO—O— in such a way that O atoms are not linked directly to one another,

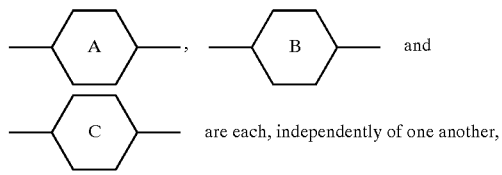

are each, independently of one another,

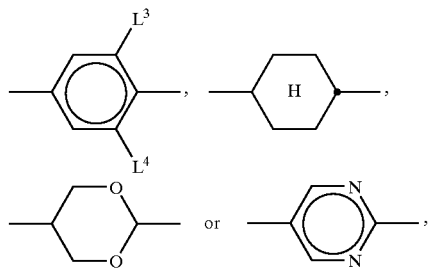

$L^1$ to $L^4$ are each, independently of one another, H or F,
$Z^1$ and $Z^2$ are each, independently of one another, —$CH_2O$—, —$OCH_2$—, —CO—O—, —$CH_2CH_2$—, —$CF_2O$—, —$OCF_2$—, —$C_2F_4$— or a single bond,
b and c are each, independently of one another, 0 or 1,
Q is —$CF_2$—, —$OCF_2$—, —CFH—, —OCFH— or a single bond, and
Y is F or Cl.
Preferred compounds of formula III are those in which $L^1$ and/or $L^2$ are F and Q—Y is F, $OCF_2H$ or $OCF_3$. Preference is furthermore given to compounds of the formula III in which $R^3$ is 1E-alkenyl or 3E-alkenyl having from 2 to 7, in particular 2, 3 or 4, carbon atoms.

Preferred compounds of the formula II are the cyano compounds of the formulae IIa to IIi

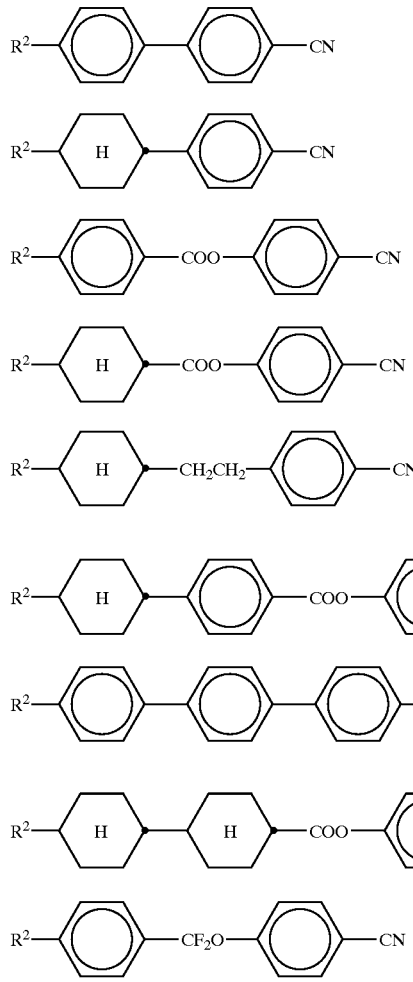

wherein $R^2$ is as defined above. $R^2$ in these compounds is preferably alkyl or alkoxy having from 1 to 8 carbon atoms.

Preference is given to mixtures which comprise one or more compounds of formulae IIa, IIb and IIg.

Preferred compounds of the formula III are compounds of formulae IIIa to IIIt

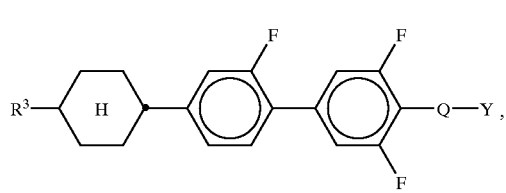

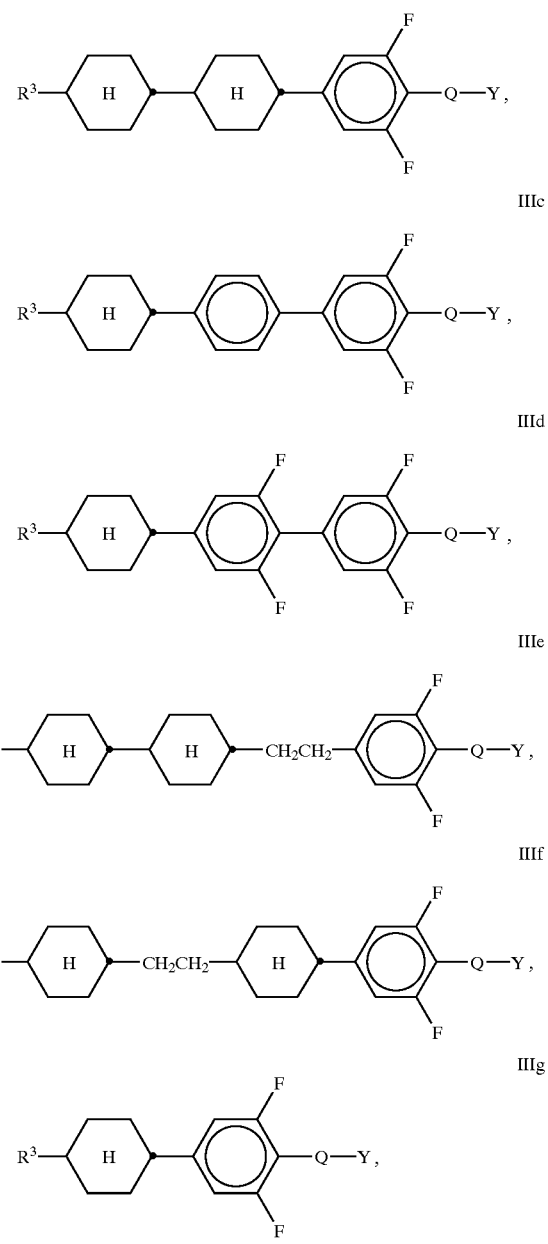

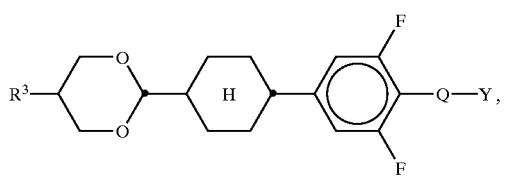

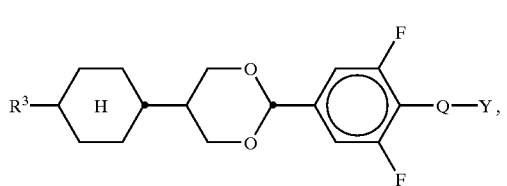

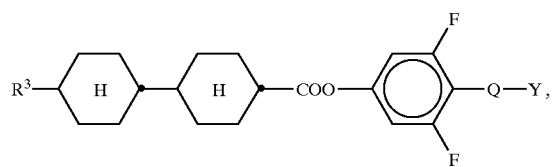

IIIj

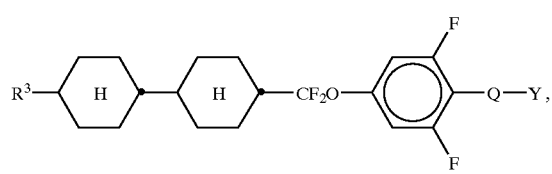

IIIk

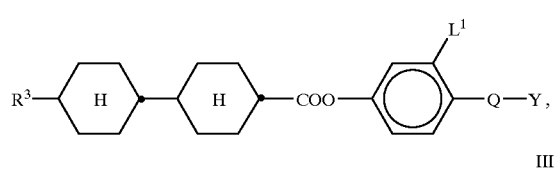

IIIl

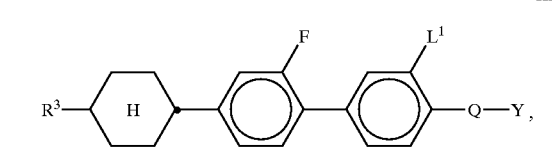

IIIm

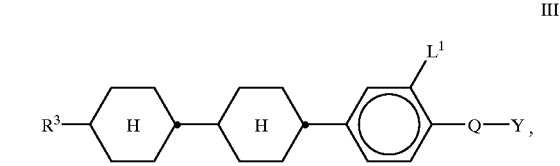

IIIn

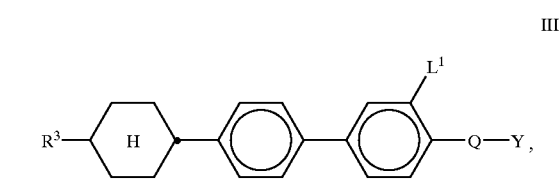

IIIo

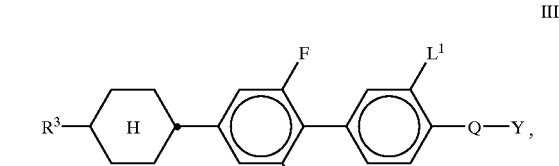

IIIp

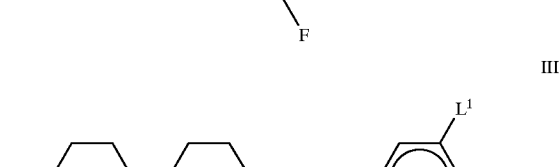

IIIq

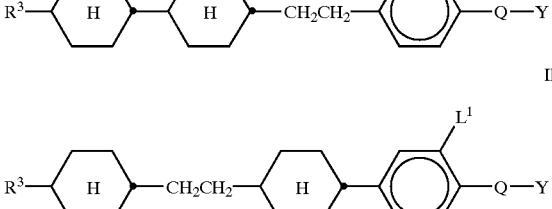

IIIr

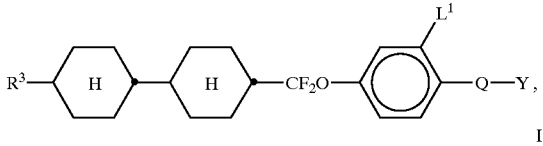

IIIs

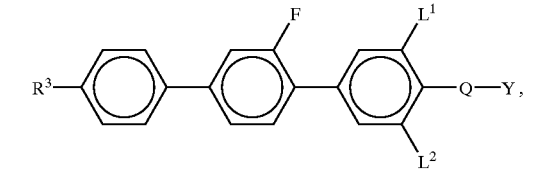

IIIt

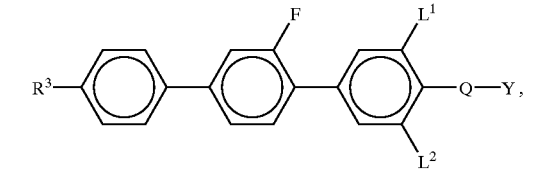

wherein $R^3$ is as defined above, and $L^1$ and $L^2$ are each, independently of one another, H or F. $R^3$ in these compounds is preferably alkyl or alkoxy having from 1 to 8 carbon atoms.

Q—Y is preferably F, Cl, $OCF_3$ or $OCHF_2$.

Media according to the invention additionally preferably comprise compounds of formulae IIIa, IIIb, IIIc, IIId, IIIe, IIIf, IIIh, IIIi, IIIj, IIIk, IIIm, IIIn, IIIp and IIIt.

In the compounds of formulae IIIa to IIIt, Q—Y is preferably F, $OCF_3$ or $OCHF_2$, furthermore Cl.

The individual compounds of formulae II and III and their sub-formulae and other compounds which can be used in the displays according to the invention, preferably TN and STN displays, are either known or can be prepared analogously to the known compounds.

The compounds of formulae II and III are to be assigned to component A.

Besides the compounds of formulae IA, IB and IC, the mixtures according to the invention preferably furthermore comprise one or more liquid-crystalline tolan compounds. Because of the high birefringence ($\Delta n$) of the tolan compounds, it is possible to use smaller layer thicknesses, thus significantly shortening the response times. The tolan compounds are preferably selected from group T containing compounds of formulae T1, T2 and/or T3:

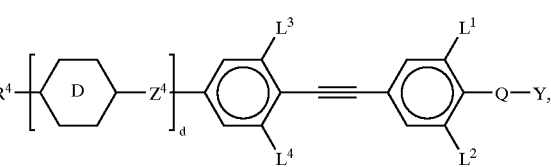

T1

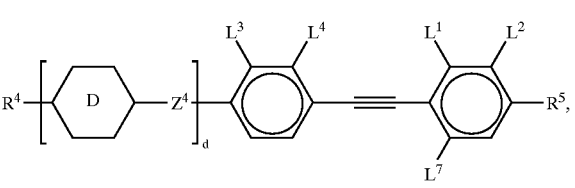

T2

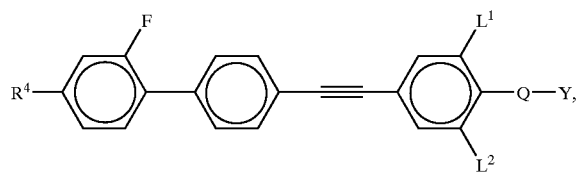
T3

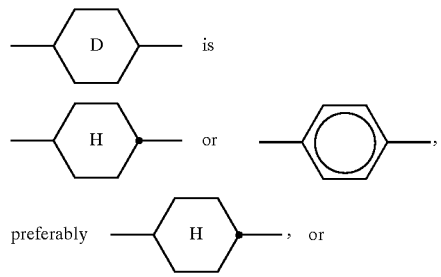
is

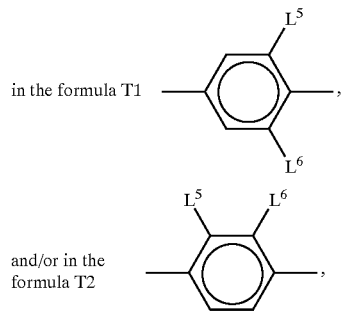

d is 0 or 1, $L^1$ to $L^7$ are each, independently of one another, H or F,

Q is —$CF_2$—, —CHF—, —$OCF_2$—, —OCHF— or a single bond,

Y is F or Cl, $Z^4$ is —CO—O—, —$CH_2CH_2$— or a single bond, $R^4$ and $R^5$ are each, independently of one another, an alkyl group having up to 12 carbon atoms which is unsubstituted or substituted by at least one halogen atom and in which one or two non-adjacent $CH_2$ groups may be replaced by —O—, —CH=CH—, —CO—, —OCO— or —CO—O— in such a way that O atoms are not linked directly to one another, where, in the case where d=1, $R^5$ may alternatively be F, Cl, $CF_3$ or $OCF_3$.

Preferred compounds of formula T1 are of sub-formulae T1a and T1b

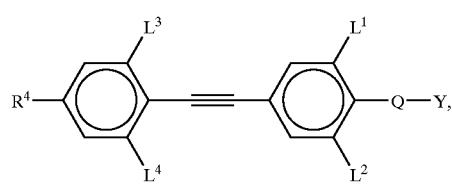
T1a

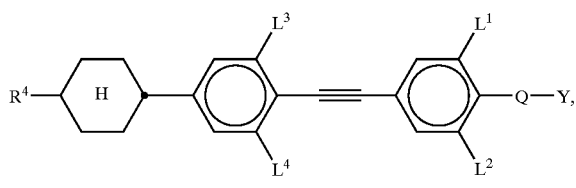
T1b wherein $L^1$ to $L^4$ and Q—Y are as defined above.

Preference is given to compounds of formula T1b-1

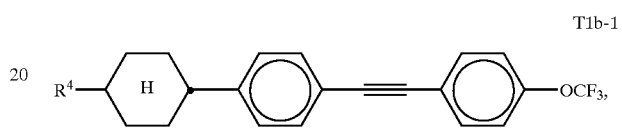
T1b-1 wherein $R^4$ is as defined above.

Preferred compounds of formula T2 are of sub-formulae T2a to T2h

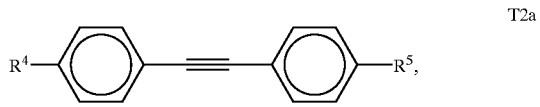
T2a

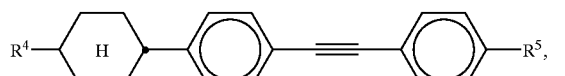
T2b

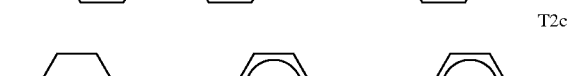
T2c

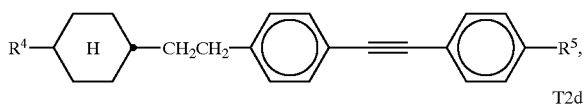
T2d

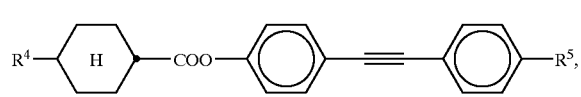
T2e

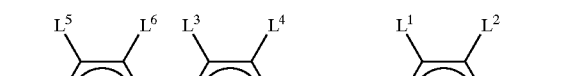
T2f

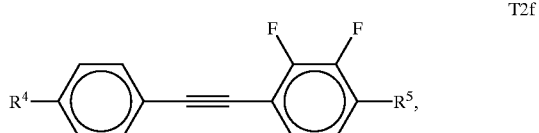
T2g

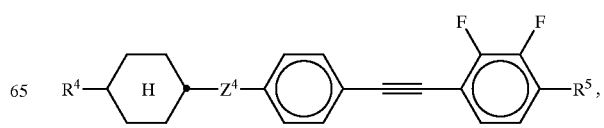

-continued

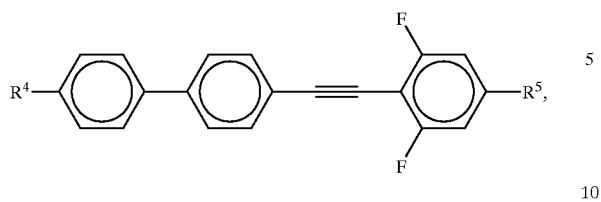

T2h wherein $R^4$, $R^5$ and $Z^4$ are as defined above, and $L^1$ to $L^6$ are each, independently of one another, H or F.

Preferred compounds of the formula T3 are of sub-formulae T3a and T3b

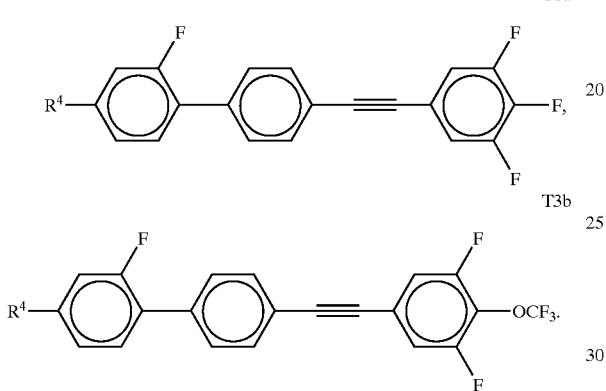

Preference is given to compounds of formulae T2a and T2b.

In a further preferred embodiment, the mixtures comprise one or more compounds of the formula T2h.

Preferred compounds of formula T2e are those in which one, two or three of the radicals $L^1$ to $L^6$ are F and the others are H, where $L^1$ and $L^2$ or $L^3$ and $L^4$ or $L^5$ and $L^6$ are not both simultaneously F.

The proportion of the compounds from the group consisting of T2a and T2b is preferably from 5 to 50%, in particular from 10 to 40%.

The proportion of the compounds of formula T2h is preferably from 2 to 35%, in particular from 4 to 25%.

The proportion of the compounds of formula T1b-1 is preferably from 2 to 25%, in particular from 4 to 15%.

The proportion of the compounds from group T is preferably from 2 to 55%, in particular from 5 to 35%.

Preferred liquid-crystal mixtures comprise one or more compounds of component A, preferably in a proportion of from 15% to 80%, particularly preferably from 20% to 70%. These compounds have a dielectric anisotropy $\Delta\epsilon$ of >1.5, preferably $\geq 3$, in particular $\Delta\epsilon>8$, particularly preferably $\Delta\epsilon \geq 12$.

Preferred liquid-crystal mixtures comprise one or more compounds of component B, preferably in a proportion of from 20 to 85%, preferably in a proportion of from 30 to 75%. The compounds of component B, in particular those containing alkenyl groups, are distinguished, in particular, by their low values for the rotational viscosity $\gamma_1$.

Compounds of formula IC are to be assigned to component B.

The mixtures according to the invention preferably comprise one or more compounds selected from the group consisting of the bicyclic compounds of formulae

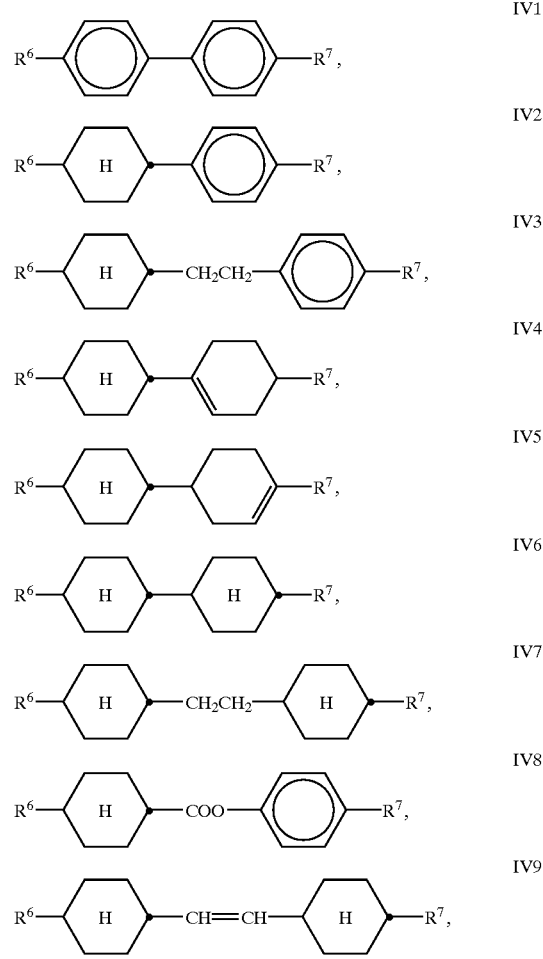

and/or one or more compounds selected from the group consisting of the tricyclic compounds of the following formulae:

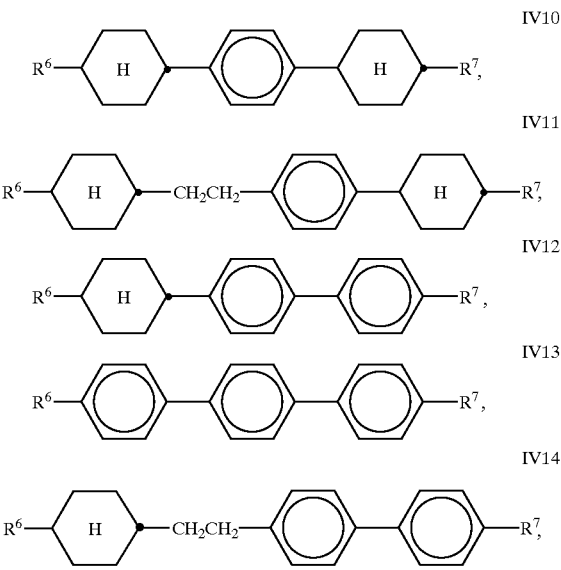

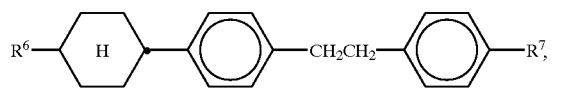 IV15

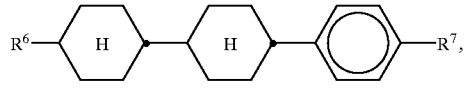 IV16

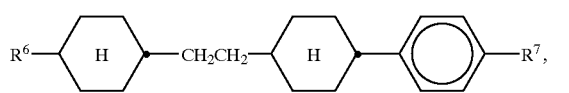 IV17

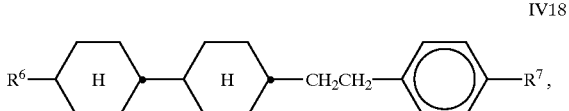 IV18

 IV19

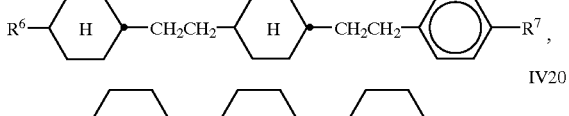 IV20

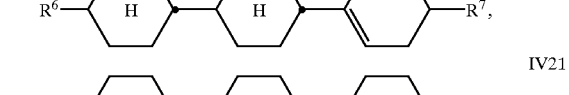 IV21

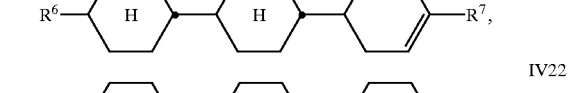 IV22

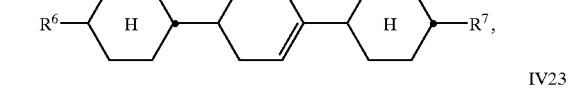 IV23

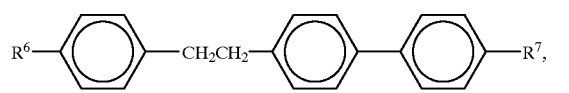 IV24

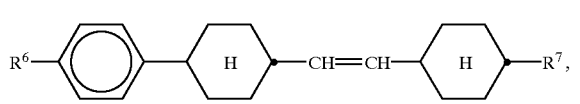 IV25

 IV26

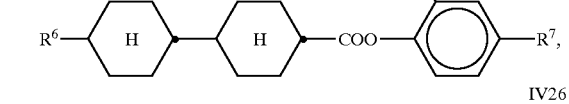

and/or one or more compounds selected from the group consisting of the tetracyclic compounds of formulae

IV27

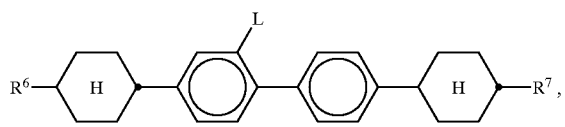

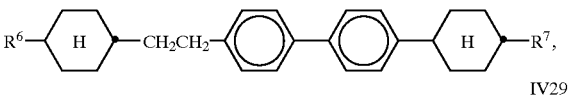 IV28

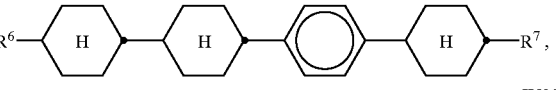 IV29

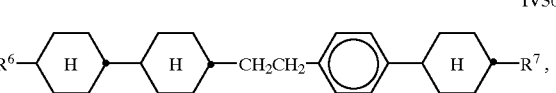 IV30

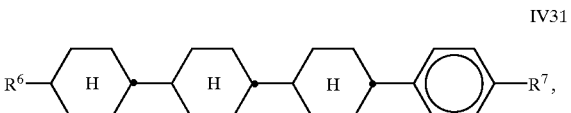 IV31

 IV32

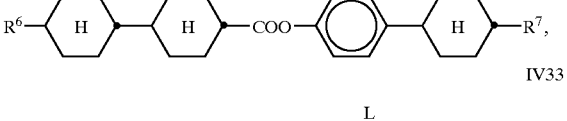 IV33

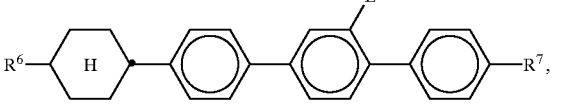

wherein $R^6$ and $R^7$ are as defined for $R^a$, L is H or F, and the 1,4-phenylene groups in IV10 to IV19 and IV23 to IV26 may each, independently of one another, also be monosubstituted or polysubstituted by fluorine.

$R^6$ and $R^7$ in the compounds of the formulae IV1 to IV35 are preferably straight-chain alkyl or alkoxy having 1 to 12 carbon atoms.

The compounds of formulae IV1 to IV33 are all to be assigned to component C.

The liquid-crystalline mixtures optionally comprise an optically active component C in an amount such that the ratio between the layer thickness and the natural pitch of the chiral nematic liquid-crystal mixture is greater than about 0.2, preferably 0.2 to 1.3. A multiplicity of chiral dopants, in some cases commercially, are available to the person skilled in the art for the component, such as, for example, cholesteryl nonanoate, S-811, from Merck KGaA, Darmstadt, and CB15 (BDH, Poole, UK). The choice of the dopant or dopants is not crucial per se.

The proportion of the compounds of component C is preferably from 0 to 10%, in particular from 0 to 5%, preferably from 0 to 3%.

The mixtures according to the invention may also optionally comprise up to 20% of one or more compounds having a dielectric anisotropy of less than −1.5 (component D).

If the mixtures comprise compounds of component D, these are preferably one or more compounds containing the structural unit 2,3-difluoro-1,4-phenylene, for example, compounds as described in DE-A 38 07 801, 38 07 861, 38 07 863, 38 07 864 and 38 07 908. Preference is given to tolans containing this structural unit as described in the International Patent Application PCT/DE 88/00133.

Further known compounds of component D are, for example, derivatives of the 2,3-dicyanohydroquinones, or cyclohexane derivatives containing the structural unit

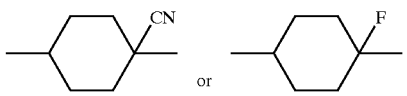

as described in DE-A 32 31 707 and DE-A 34 07 013.

The liquid-crystal displays according to the invention preferably comprise no compounds of component D.

The term "alkenyl" in the definitions of $R^a$, $R^b$, $R^c$, and $R^1$–$R^7$ covers straight-chain and branched alkenyl groups, preferably having 2–7 carbon atoms, in particular the straight-chain groups. Preferred alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl.

Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

In preferred embodiments, the mixtures comprise from 5 to 30% by weight, in particular from 8 to 20%, of one or more compounds of formula IA;

from 10 to 40% by weight, in particular from 10 to 30% by weight, of one or more compounds of formula IB;

from 25 to 60% by weight, in particular from 25 to 50%, of one or more compounds of formula IC;

one or more, preferably one, two or three, tolan compounds of formula T2h

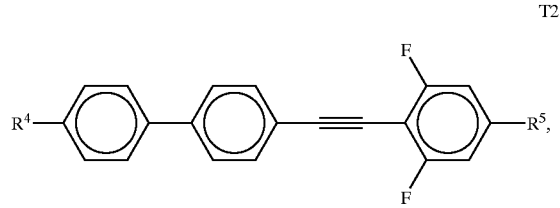

T2h wherein $R^4$ and $R^5$ are as defined above;

one or more, preferably in each case from two to four, tolan compounds of the following formulae:

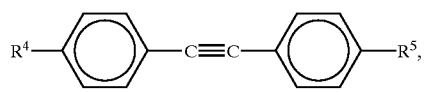
T2a

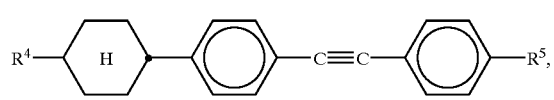
T2b

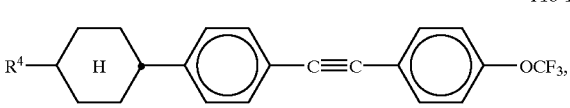
T1b-1 wherein $R^4$ and $R^5$ are as defined above;
one or more compounds of the following formulae:

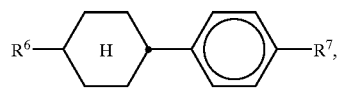
IV2

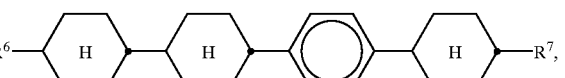
IV27

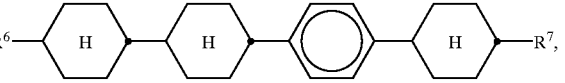
IV29 wherein $R^6$, $R^7$ and L are as defined above. L in formula IV27 is preferably F;

one or more, in particular from two to five, compounds selected from the group consisting of the compounds IIIa to IIIg;

at least two compounds selected from the following group consisting of the compounds

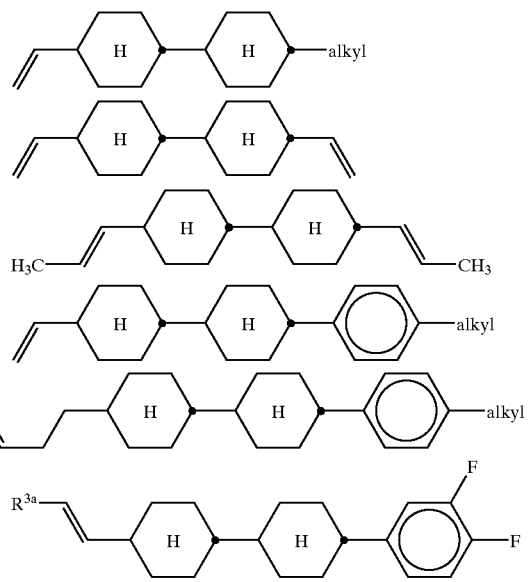

wherein alkyl is an alkyl group having 1 to 8 carbon atoms, and $R^{3a}$ is H, $CH_3$, $C_2H_5$ or n—$C_3H_7$;

more than 20% of compounds having positive dielectric anisotropy, in particular having $\Delta\epsilon \geq +12$.

The mixtures according to the invention are distinguished, in particular on use in TN and STN displays of high layer thicknesses, by very low total response times ($t_{tot}=t_{on}+t_{off}$).

The liquid-crystal mixtures used in the TN and STN cells according to the invention are dielectrically positive, with $\Delta\epsilon \geq 1$. Preference is given to liquid-crystal mixtures with $\Delta\epsilon \geq 3$, in particular with $\Delta\epsilon \geq 5$.

The liquid-crystal mixtures according to the invention have favorable values for the threshold voltage $V_{10/02/20}$ and for the rotational viscosity $\gamma_1$. If the value for the optical path difference d·$\Delta$n is prespecified, the value for the layer thickness d is determined by the optical anisotropy $\Delta$n. In particular at relatively high values for d·$\Delta$n, the use of liquid-crystal mixtures according to the invention that have a relatively high value for the optical anisotropy is generally preferred, since the value for d can then be selected to be relatively small, which results in more favorable values for the response times. However, liquid-crystal displays according to the invention which contain liquid-crystal mixtures according to the invention with smaller values for Δn are also characterised by advantageous values for the response times.

The liquid-crystal mixtures according to the invention are furthermore characterised by advantageous values for the steepness of the electro-optical characteristic line, and can be operated with high multiplex rates, in particular at temperatures above 20° C. In addition, the liquid-crystal mixtures according to the invention have high stability and favorable values for the electrical resistance and the frequency dependence of the threshold voltage. The liquid-crystal displays according to the invention have a large working-temperature range and good angle dependence of the contrast.

The construction of the liquid-crystal display elements according to the invention from polarisers, electrode base plates and electrodes having a surface treatment such that the preferential alignment (director) of the liquid-crystal molecules in each case adjacent thereto is usually twisted by a value of from 160° to 720° from one electrode to the other corresponds to the usual structure for display elements of this type. The term "usual structure" here is broadly drawn and also covers all derivatives and modifications of the TN and STN cell, in particular also matrix display elements and display elements containing additional magnets.

The surface tilt angle at the two outer plates may be identical or different. Identical tilt angles are preferred. Preferred TN displays have pre-tilt angles between the longitudinal axis of the molecules at the surface of the outer plates and the outer plates of from 0° to 7°, preferably from 0.01° to 5° in particular from 0.1° to 2°. In the STN displays, the pre-tilt angle is from 1° to 30°, preferably from 1° to 12° and in particular from 3° to 10°.

The twist angle of the TN mixture in the cell has a value of between 22.5° and 170°, preferably between 45° and 130° and in particular between 80° and 115°. The twist angle of the STN mixture in the cell from alignment layer to alignment layer has a value of between 100° and 600°, preferably between 170° and 300° and in particular between 180° and 270°.

The liquid-crystal mixtures which can be used in accordance with the invention are prepared in a manner which is conventional per se. In general, the desired amount of the components used in lesser amount are dissolved in the components making up the principal constituent, advantageously at elevated temperature. It is also possible to mix solutions of the components in an organic solvent, for example in acetone, chloroform or methanol, and to remove the solvent again, for example, by distillation, after thorough mixing.

The dielectrics may also comprise further additives which are known to the person skilled in the art and are described in prior art literature. For example, 0–15% of pleochroic dyes may be added.

In the present application and in the examples below, the structures of the liquid-crystal compounds are indicated by means of acronyms, the transformation into chemical formulae taking place in accordance with Tables A and B. All radicals $C_nH_{2n+1}$ and $C_mH_{2m+1}$ are straight-chain alkyl radicals having n and m carbon atoms respectively (n and m=1–12). The alkenyl radicals have the trans-configuration. The coding in Table B is self-evident. In Table A, only the acronym for the parent structure is indicated.

In individual cases, the acronym for the parent structure is followed, separated by a dash, by the code indicated in the table below for the substituents $R^{1*}$, $R^{2*}$, $L^1$, $L^2$ and $L^3$.

| Code for $R^{1*}$, $R^{2*}$, $L^1$, $L^2$, $L^3$ | $R^{1*}$ | $R^{2*}$ | $L^1$ | $L^2$ | $L^3$ |
|---|---|---|---|---|---|
| nm | $C_nH_{2n+1}$ | $C_mH_{2m+1}$ | H | H | H |
| nOm | $OC_nH_{2n+1}$ | $C_mH_{2m+1}$ | H | H | H |
| nO.m | $C_nH_{2n+1}$ | $OC_mH_{2m+1}$ | H | H | H |
| n | $C_nH_{2n+1}$ | CN | H | H | H |
| nN.F | $C_nH_{2n+1}$ | CN | H | H | F |
| nN.F.F | $C_nH_{2n+1}$ | CN | H | F | F |
| nF | $C_nH_{2n+1}$ | F | H | H | H |
| nCl | $OC_nH_{2n+1}$ | Cl | H | H | H |
| nOF | $OC_nH_{2n+1}$ | F | H | H | H |
| nF.F | $C_nH_{2n+1}$ | F | H | H | F |
| nF.F.F | $C_nH_{2n+1}$ | F | H | F | F |
| nmF | $C_nH_{2n+1}$ | $C_mH_{2m+1}$ | F | H | H |
| nOCF$_3$ | $C_nH_{2n+1}$ | OCF$_3$ | H | H | H |
| nOCF$_2$ | $C_nH_{2n+1}$ | OCHF$_2$ | H | H | H |
| n-Vm | $C_nH_{2n+1}$ | —CH=CH—$C_mH_{2m+1}$ | H | H | H |
| nV-Vm | $C_nH_{2n+1}$ —CH=CH— | —CH=CH—$C_mH_{2m+1}$ | H | H | H |
| nS | $C_nH_{2n+1}$ | NCS | H | H | H |

The mixtures according to the invention preferably comprise one or more compounds from Tables A and B.

TABLE A ($L^1$, $L^2$, $L^3$ = H or F)

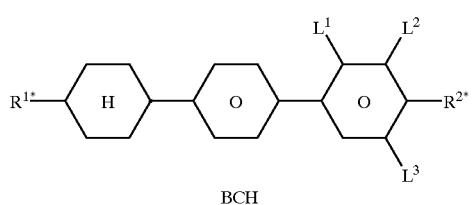

BCH

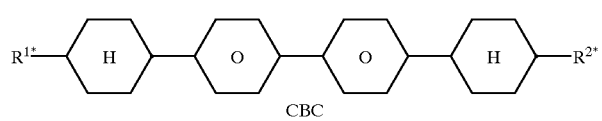

CBC

TABLE A-continued
($L^1, L^2, L^3$ = H or F)
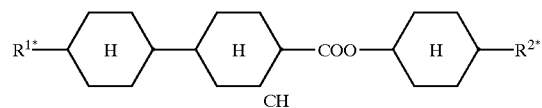
CH
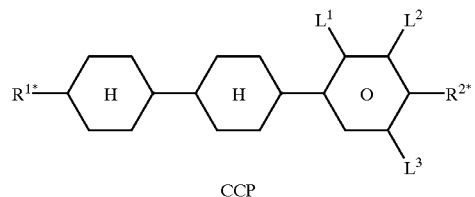
CCP
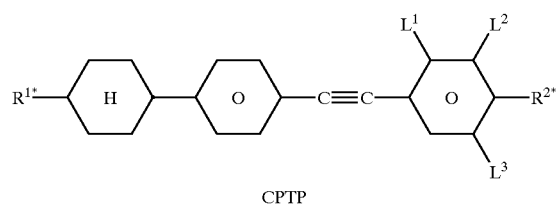
CPTP
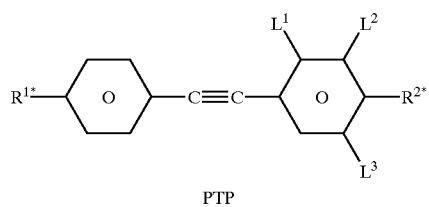
PTP
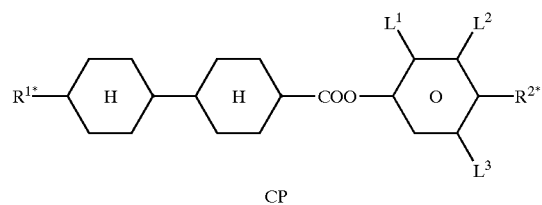
CP
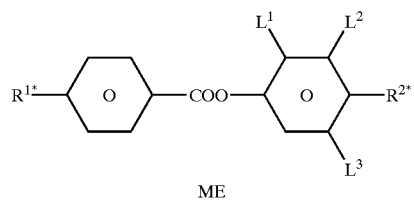
ME
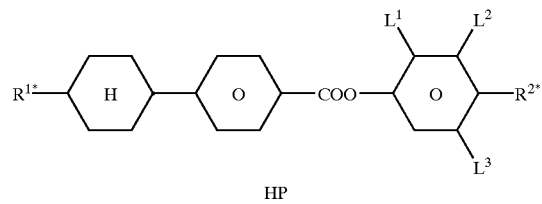
HP
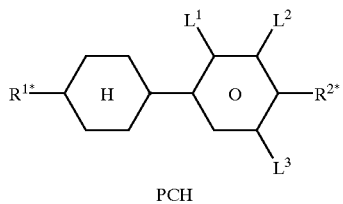
PCH
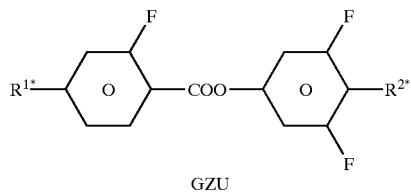
GZU
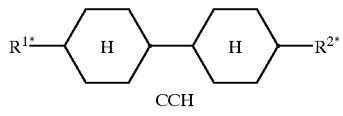
CCH
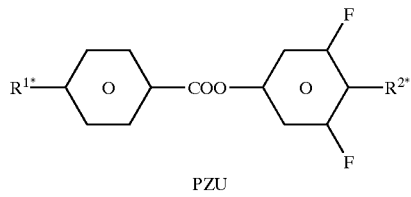
PZU
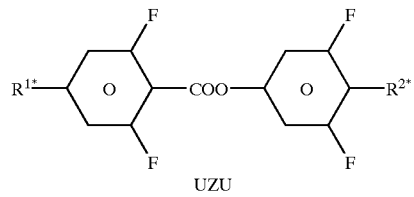
UZU
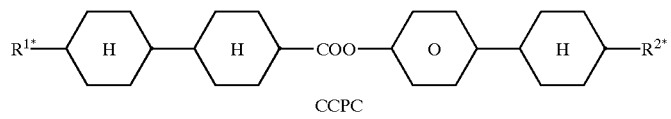
CCPC TABLE A-continued
$(L^1, L^2, L^3 = H \text{ or } F)$
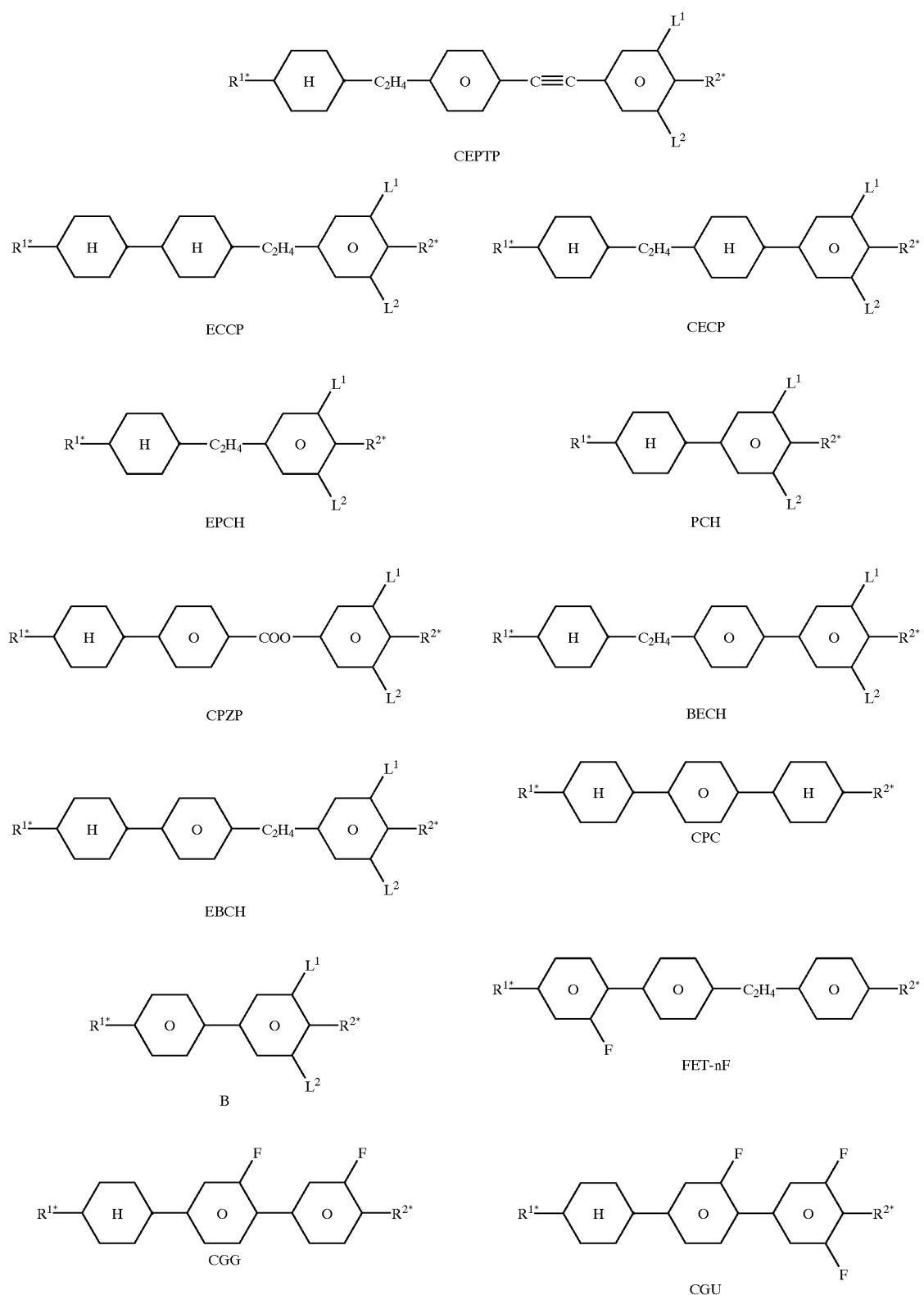

TABLE A-continued
($L^1$, $L^2$, $L^3$ = H or F)
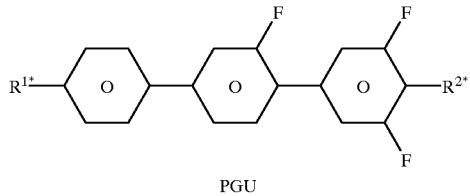
PGU
TABLE B
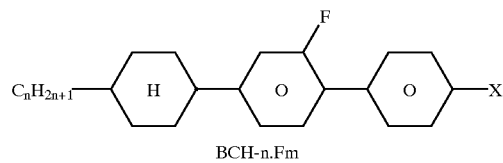
BCH-n.Fm
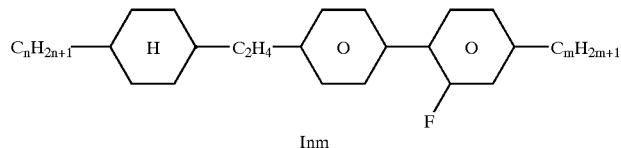
Inm
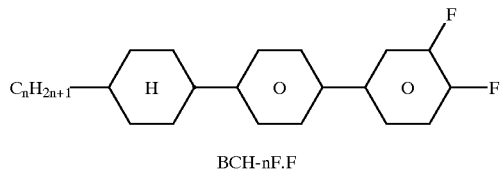
BCH-nF.F
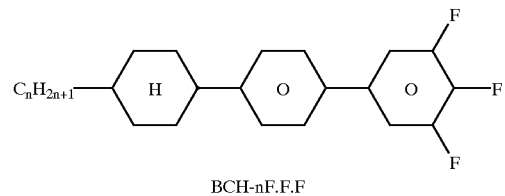
BCH-nF.F.F
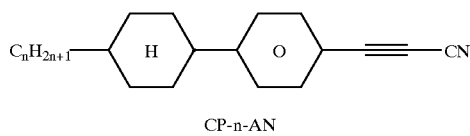
CP-n-AN
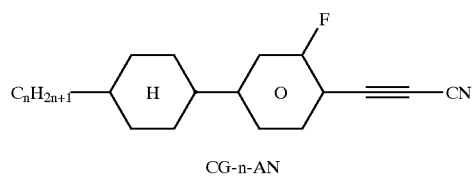
CG-n-AN
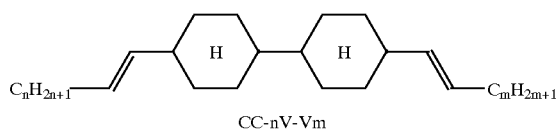
CC-nV-Vm
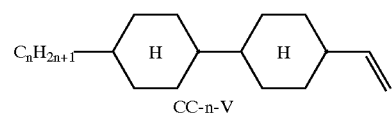
CC-n-V
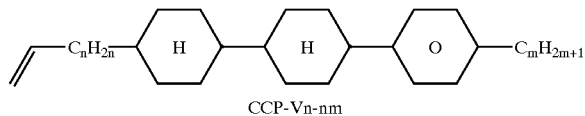
CCP-Vn-nm
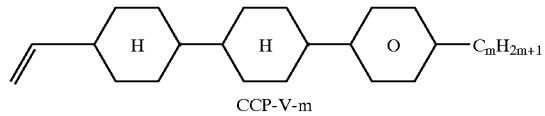
CCP-V-m
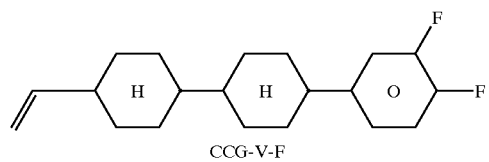
CCG-V-F
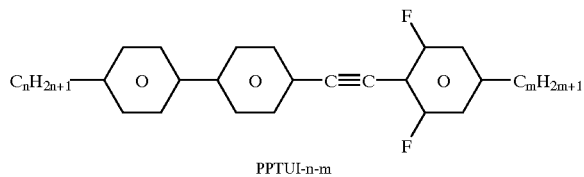
PPTUI-n-m TABLE B-continued
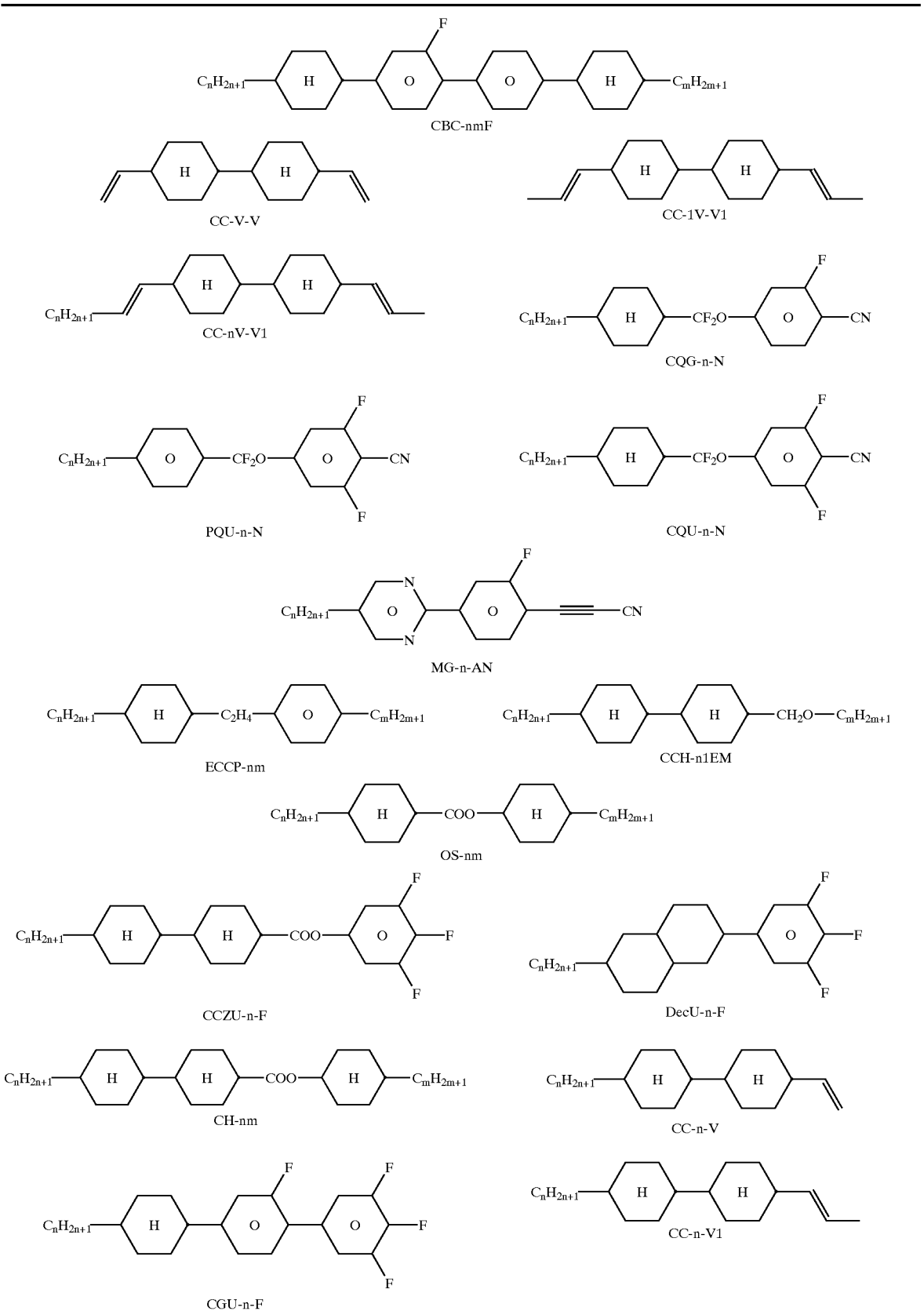

TABLE B-continued

CPTU-n-F, GPTU-n-F (structural formulas)

The following examples are intended to illustrate the invention without representing a limitation. The following abbreviations are used:

cl.p. clearing point (nematic-isotropic phase transition temperature),

S-N smectic-nematic phase transition temperature, visc. flow viscosity (mm²/s, at 20° C. unless stated otherwise), Δn optical anisotropy (589 nm, 200° C.)

S characteristic line steepness=$V_{90}/N_{10}$ $V_{10}$ threshold voltage=characteristic voltage at a relative contrast of 10%, $V_{90}$ characteristic voltage at a relative contrast of 90%, $$t_{ave} \quad \frac{t_{on} + t_{off}}{2} \quad \text{(mean response time)}$$

$t_{on}$ time from switching on until 90% of the maximum contrast is reached, $t_{off}$ time from switching off until 10% of the maximum contrast is reached, mux multiplex rate $t_{store}$ low-temperature storage stability in hours (−20° C., −30° C., −40° C.)

In the foregoing and in the following examples, all temperatures are given in degrees C. The percentages are by weight. All values relate to 20° C., unless stated otherwise. The displays are addressed, unless stated otherwise, at a multiplex rate of 1/240 and a bias of 1/16. The twist is 240°, unless stated otherwise.

The entire disclosure of all applications, patents and publications, cited above and below, and of corresponding German Application No. 10136750.3, filed Jul. 27, 2001 is hereby incorporated by reference.

EXAMPLE 1

| | | | |
|---|---|---|---|
| ME2N.F | 5.0% | Clearing point [° C.]: | 83.4 |
| ME3N.F | 6.0% | Δn [589 nm, 20° C.]: | 0.1316 |
| ME4N.F | 9.0% | Δε [1 kHz; 20° C.]: | 19.1 |
| CG-3-AN | 10.0% | $γ_1$ [mPa · s]: | 153 |
| PCH-3N.F.F | 13.0% | | |
| CCG-V-F | 21.0% | | |
| CCPC-33 | 5.0% | | |
| CCPC-34 | 5.0% | | |
| CPTU-3-F | 10.0% | | |
| CCP-V-1 | 14.0% | | |
| CC-5-V | 2.0% | | |

EXAMPLE 2

| | | | |
|---|---|---|---|
| ME2N.F | 5.0% | Clearing point [° C.]: | 83.8 |
| ME3N.F | 6.0% | Δn [589 nm, 20° C.]: | 0.1322 |
| ME4N.F | 9.0% | Δε [1 kHz; 20° C.]: | 19.1 |
| CG-3-AN | 10.0% | $γ_1$ [mPa · s]: | 154 |
| PCH-3N.F.F | 13.0% | | |
| CCG-V-F | 21.0% | | |
| CCPC-33 | 5.0% | | |
| CCPC-34 | 5.0% | | |
| GPTU-3-F | 6.0% | | |
| CCP-V-1 | 17.0% | | |
| CC-5-V | 3.0% | | |

EXAMPLE 3

| | | | |
|---|---|---|---|
| ME2N.F | 6.0% | Clearing point [° C.]: | 83.1 |
| ME3N.F | 6.0% | Δn [589 nm, 20° C.]: | 0.1339 |
| ME4N.F | 10.0% | Δε [1 kHz; 20° C.]: | 19.2 |
| CG-3-AN | 10.0% | $γ_1$ [mPa · s]: | 146 |
| PCH-3N.F.F | 13.0% | | |
| CC-5-V | 11.0% | | |
| CCG-V-F | 21.0% | | |
| CCPC-33 | 5.0% | | |
| CCPC-34 | 5.0% | | |
| CCPC-35 | 5.0% | | |
| PPTUI-3-2 | 6.0% | | |
| CCP-V-1 | 2.0% | | |

EXAMPLE 4

| | | | |
|---|---|---|---|
| ME2N.F | 5.0% | Clearing point [° C.]: | 83.1 |
| ME3N.F | 5.0% | Δn [589 nm, 20° C.]: | 0.1344 |
| ME4N.F | 8.0% | Δε [1 kHz; 20° C.]: | 19.1 |
| MG-5-AN | 9.0% | $γ_1$ [mPa · s]: | 138 |
| PCH-3N.F.F | 13.0% | | |
| CC-5-V | 18.0% | | |
| CCG-V-F | 21.0% | | |
| CCPC-33 | 5.0% | | |
| CCPC-34 | 5.0% | | |
| CCPC-35 | 5.0% | | |
| PPTUI-3-2 | 6.0% | | |

EXAMPLE 5

| | | | |
|---|---|---|---|
| ME2N.F | 3.0% | Clearing point [° C.]: | 94.8 |
| ME3N.F | 4.0% | Δn [589 nm, 20° C.]: | 0.1355 |
| ME4N.F | 10.0% | Δε [1 kHz; 20° C.]: | 13.7 |
| CG-3-AN | 8.0% | $γ_1$ [mPa · s]: | 130 |
| CC-5-V | 19.0% | | |

-continued

| | |
|---|---|
| CCG-V-F | 20.0% |
| CCP-V-1 | 10.0% |
| CCP-V2-1 | 7.0% |
| CCPC-33 | 4.0% |
| CCPC-34 | 3.0% |
| GPTU-3-F | 10.0% |
| PTP-102 | 2.0% |

EXAMPLE 6

| | | | |
|---|---|---|---|
| ME2N.F | 3.0% | Clearing point [° C.]: | 95.4 |
| ME3N.F | 3.0% | Δn [589 nm, 20° C.]: | 0.1354 |
| ME4N.F | 12.0% | Δε [1 kHz; 20° C.]: | 13.7 |
| CG-3-AN | 8.0% | γ₁ [mPa · s]: | 127 |
| CC-5-V | 18.0% | | |
| CCG-V-F | 20.0% | | |
| CCP-V-1 | 10.0% | | |
| CCP-V2-1 | 6.0% | | |
| CBC-33 | 4.0% | | |
| CBC-53 | 3.0% | | |
| CPTU-3-F | 10.0% | | |
| PTP-102 | 3.0% | | |

EXAMPLE 7

| | | | |
|---|---|---|---|
| ME2N.F | 4.0% | Clearing point [° C.]: | 95.0 |
| ME3N.F | 4.0% | Δn [589 nm, 20° C.]: | 0.1368 |
| ME4N.F | 12.0% | Δε [1 kHz; 20° C.]: | 13.7 |
| CG-3-AN | 8.0% | γ₁ [mPa · s]: | 113 |
| CC-5-V | 23.0% | | |
| CCG-V-F | 20.0% | | |
| CCP-V-1 | 13.0% | | |
| CCPC-33 | 3.0% | | |
| CCPC-34 | 3.0% | | |
| PPTUI-3-2 | 10.0% | | |

EXAMPLE 8

| | | | |
|---|---|---|---|
| ME2N.F | 3.0% | Clearing point [° C.]: | 95.5 |
| ME3N.F | 3.0% | Δn [589 nm, 20° C.]: | 0.1369 |
| ME4N.F | 10.0% | Δε [1 kHz; 20° C.]: | 13.7 |
| MG-5-AN | 8.0% | γ₁ [mPa · s]: | 113 |
| PCH-302 | 6.0% | | |
| CCG-V-F | 20.0% | | |
| CCP-V-1 | 15.0% | | |
| CCPC-33 | 3.0% | | |
| CCPC-34 | 3.0% | | |
| PPTUI-3-2 | 8.0% | | |
| CC-5-V | 21.0% | | |

EXAMPLE 9

| | | | |
|---|---|---|---|
| ME2N.F | 6.0% | Clearing point [° C.]: | 84.1 |
| ME3N.F | 6.0% | Δn [589 nm, 20° C.]: | 0.1316 |
| ME4N.F | 10.0% | Δε [1 kHz; 20° C.]: | 19.1 |
| CG-3-AN | 10.0% | γ₁ [mPa · s]: | 153 |
| PCH-3N.F.F | 13.0% | | |
| CC-5-V | 10.5% | | |
| CCG-V-F | 21.0% | | |
| CCPC-33 | 4.0% | | |

-continued

| | |
|---|---|
| CCPC-34 | 4.0% |
| CBC-33F | 3.0% |
| CPTP-301 | 3.5% |
| CPTP-302 | 4.0% |
| CCP-V-1 | 5.0% |

EXAMPLE 10

| | | | |
|---|---|---|---|
| ME2N.F | 4.25% | Clearing point [° C.]: | 95.3 |
| ME3N.F | 4.25% | Δn [589 nm, 20° C.]: | 0.1371 |
| ME4N.F | 12.00% | Δε [1 kHz; 20° C.]: | 13.7 |
| CG-3-AN | 8.00% | γ₁ [mPa · s]: | 121 |
| CC-5-V | 19.50% | | |
| CCG-V-F | 20.00% | | |
| CCP-V-1 | 10.00% | | |
| CCP-V2-1 | 8.50% | | |
| CBC-33F | 3.00% | | |
| PTP-102 | 4.50% | | |
| CPTP-301 | 3.00% | | |
| CPTP-302 | 3.00% | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A liquid-crystal mixture comprising at least one compound of formula IA,

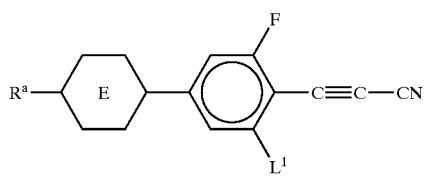

IA one or more compounds of formula IB,

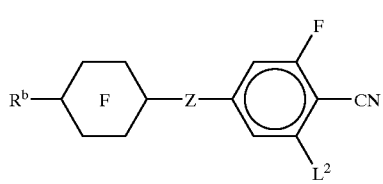

IB and one or more compounds of formula IC,

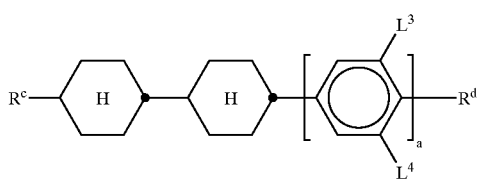

IC

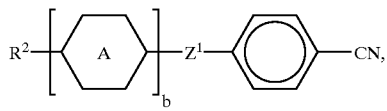

II

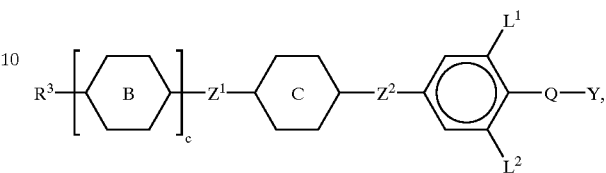

III wherein $R^a$, $R^b$ and $R^d$ are each, independently of one another, an alkyl group having 1 to 12 carbon atoms that is unsubstituted or substituted by at least one halogen atom and wherein one or two non-adjacent CH$_2$ groups are optionally replaced by —O—, —CH=CH—, —CO—, —OCO— or —CO—O— in a manner that O atoms are not linked directly to one another, and wherein when a=1, $R^d$ is optionally F, Cl, OCHFCF$_3$, CF$_3$ or OCF$_3$, $R^c$ is alkenyl or alkenyloxy having 2 to 6 carbon atoms, wherein $R^2$ and $R^3$ are each, independently of one another, an alkyl or alkoxy group having 1 to 12 carbon atoms or an alkenyl group having 2 to 12 carbon atoms, wherein one or two non-adjacent CH$_2$ groups are optionally replaced by —O—, —CH=CH—, —CO—, —OCO— or —CO—O— in a manner that O atoms are not linked directly to one another,

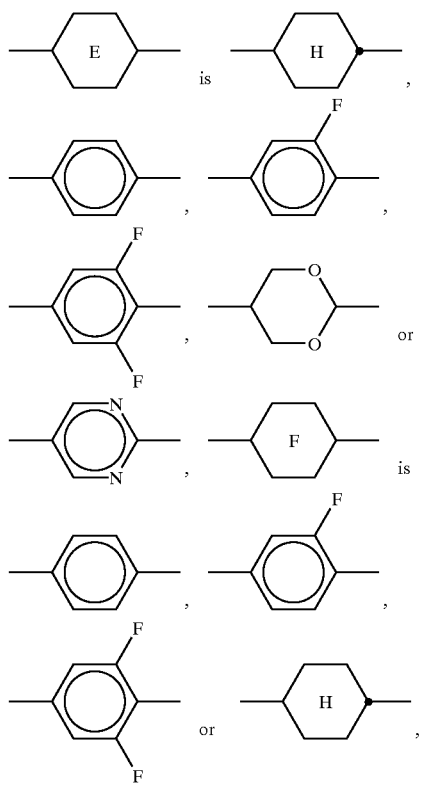

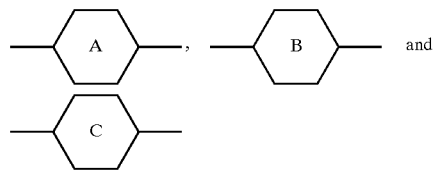

are each, independently of one another,

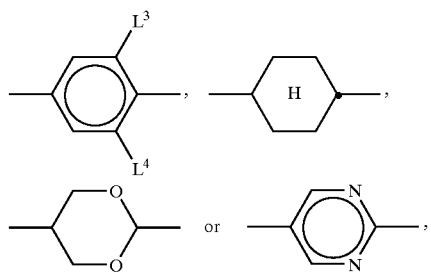

$L^1$ to $L^4$ are each, independently of one another, H or F, $Z^1$ and $Z^2$ are each, independently of one another, —CH$_2$O—, —OCH$_2$—, —CO—O—, —CH$_2$CH$_2$—, —CF$_2$O—, —OCF$_2$—, —C$_2$F$_4$— or a single bond, b and c are each, independently of one another, 0 or 1, Q is —CF$_2$—, —OCF$_2$—, —CFH—, —OCFH— or a single bond, and Y is F or Cl.

Z is —CF$_2$O—, —OCF$_2$— or a single bond, $L^1$ to $L^4$ are each, independently of one another, H or F, and a is 0 or 1, wherein the mixture comprises at least 25% by weight of a compound of formula IC.

2. A liquid-crystal mixture according to claim 1 further comprising one or more compounds of formulae II or III, or II and III,

3. A liquid-crystal mixture according to claim 1 further comprising one or more compounds of formulae T1, T2 and T3

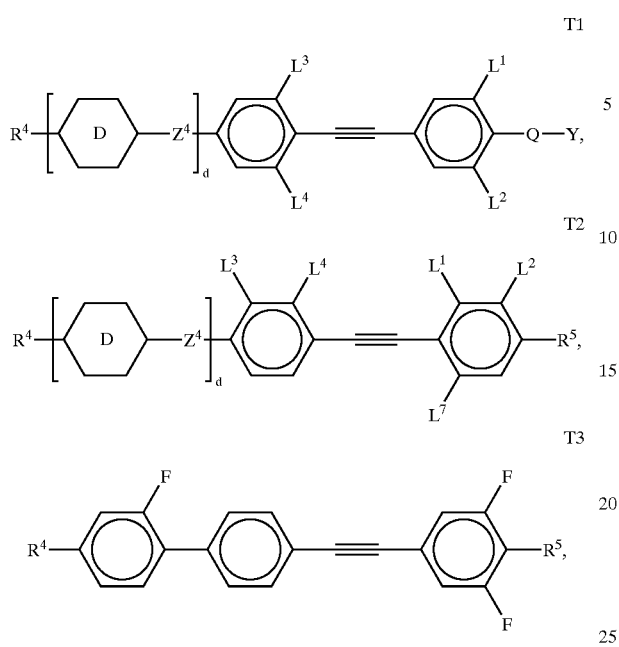

wherein

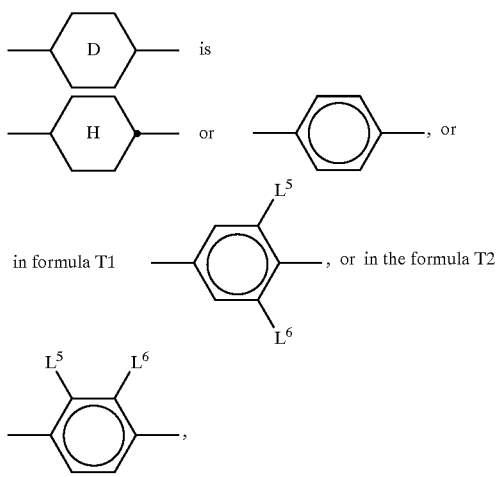

d is 0 or 1,
L¹ to L⁷ are each, independently of one another, H or F,
Q is —CF₂—, —CHF—, —OCF₂—, —OCHF— or a single bond,
Y is F or Cl,
Z⁴ is —CO—O—, —CH₂CH₂— or a single bond,
R⁴ and R⁵ are each, independently of one another, an alkyl group having from 1 to 12 carbon atoms that is unsubstituted or substituted by at least one halogen atom and wherein one or two non-adjacent CH₂ groups are optionally replaced by —O—, —CH=CH—, —CO—, —OCO— or —CO—O— in a manner that O atoms are not linked directly to one another, wherein when d=1, R⁵ is optionally F, Cl, CF₃ or OCF₃.

4. A TN IPS or STN liquid-crystal display comprising
two outer plates, which, together with a frame, form a cell,
a chiral nematic liquid-crystal mixture of positive dielectric anisotropy located in the cell,
electrode layers with alignment layers on the insides of the outer plates,
a tilt angle between the longitudinal axis of the molecules at the surface of the outer plates and the outer plates of from 0 degree to 30 degrees, and
a twist angle of the liquid-crystal mixture in the cell from alignment layer to alignment layer with a value of between 22.50° and 600°,
the chiral nematic liquid-crystal mixture comprising
a) 15–80% by weight of a liquid-crystalline component A containing one or more compounds having a dielectric anisotropy of greater than 1.5;
b) 20–85% by weight of a liquid-crystalline component B containing one or more compounds having a dielectric anisotropy of between −1.5 and 1.5;
c) 0–20% by weight of a liquid-crystalline component D containing one or more compounds having a dielectric anisotropy of below −1.5, and
d) optionally, an optically active component C in an amount whereby the ratio between the layer thickness and the natural pitch of the chiral nematic liquid-crystal mixture is greater than about 0.2.
wherein the liquid-crystal mixture comprises at least one compound of formula IA,

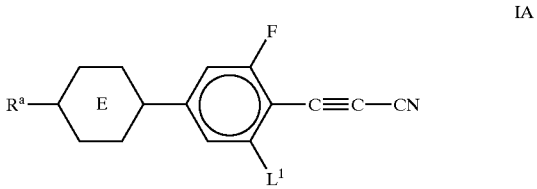

one or more compounds of formula IB,

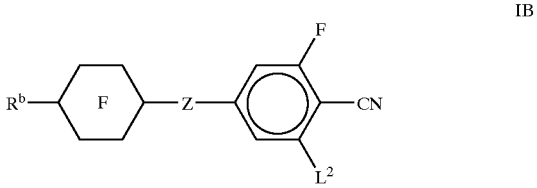

and
one or more compounds of formula IC,

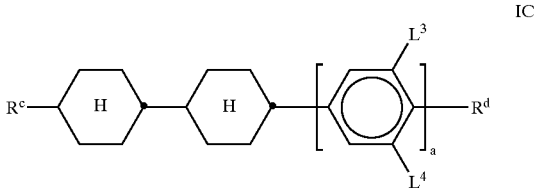

wherein
Rᵃ, Rᵇ
and Rᵈ are each, independently of one another, an alkyl group having 1 to 12 carbon atoms that is unsubstituted or substituted by at least one halogen atom and wherein one or two non-adjacent CH₂ groups are optionally replaced by —O—, —CH=CH—, —CO—, —OCO— or —CO—O— in a manner that O atoms are not linked directly to one another, and wherein when a=1, Rᵈ is optionally F, Cl, CF₃ or OCF₃,
Rᶜ is alkenyl or alkenyloxy having from 2 to 6 carbon atoms,

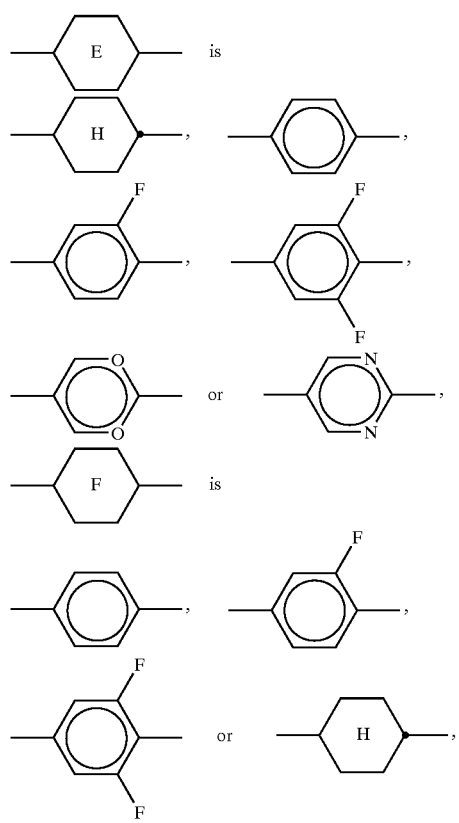

Z is —CF$_2$O—, —OCF$_2$— or a single bond,

L$^1$ to L$^4$ are each, independently of one another, H or F, and a is 0 or 1, wherein the mixture comprises at least 25% by weight of a compound of formula IC.

5. A liquid-crystal display according to claim 4, wherein component A comprises one or more compounds of formulae IIa to IIi

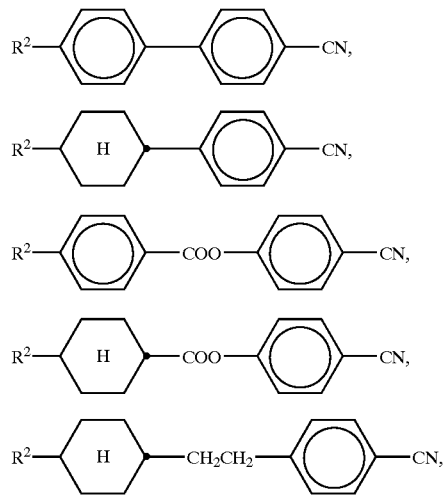

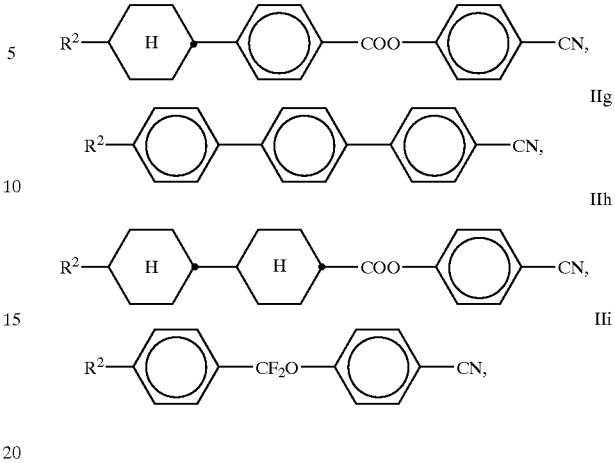

wherein

R$^2$ is an alkyl or alkoxy group having 1 to 12 carbon atoms or an alkenyl group having 2 to 12 carbon atoms, wherein one or two non-adjacent CH$_2$ groups are optionally replaced by —O—, —CH=CH—, —CO—, —OCO— or —CO—O— in a manner that O atoms are not linked directly to one another.

6. A liquid-crystal display according to claim 4, wherein component A comprises one or more compounds of formulae IIIa to IIIt

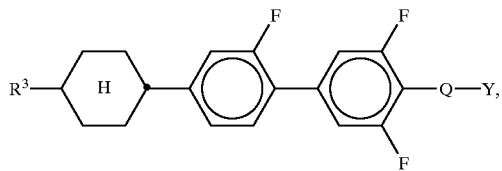

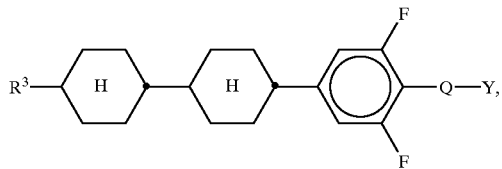

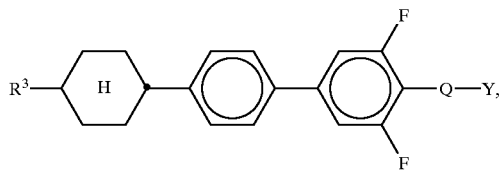

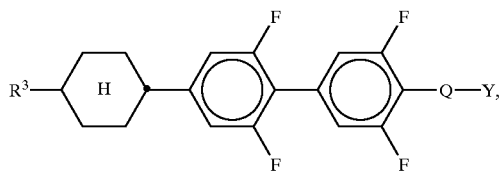

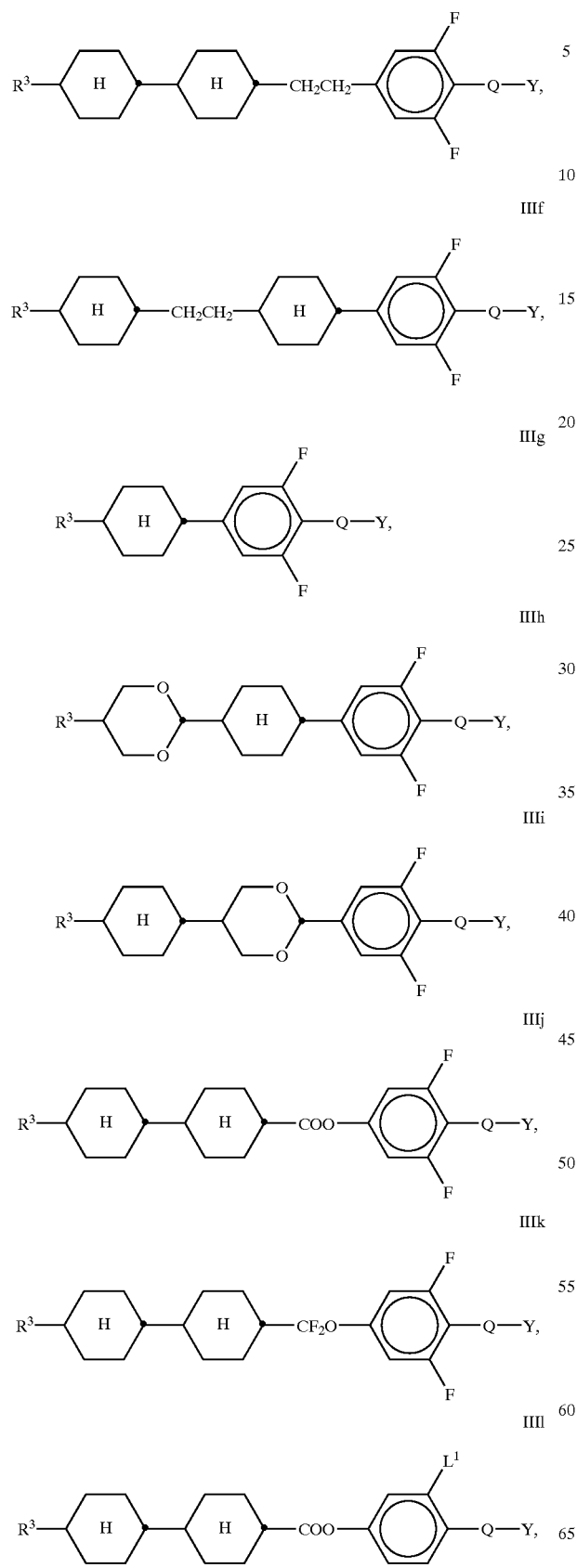
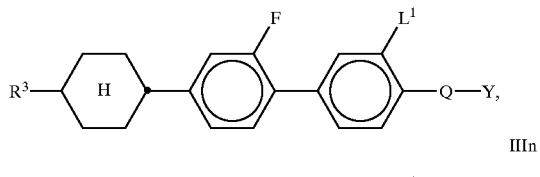
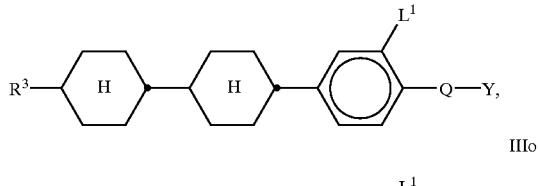
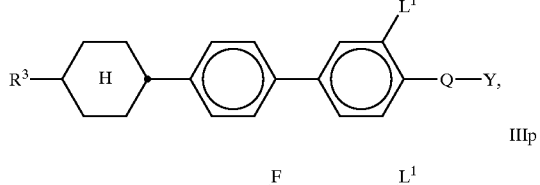
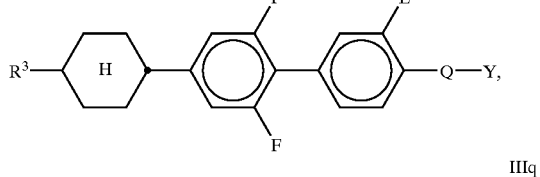
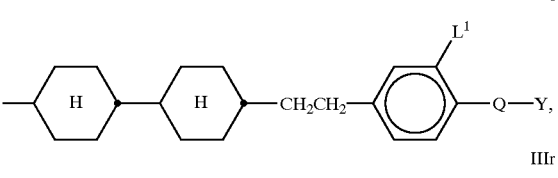
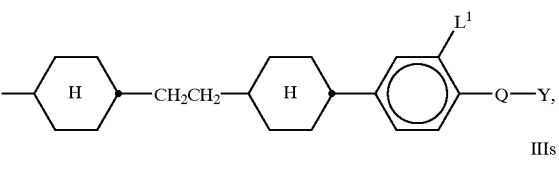
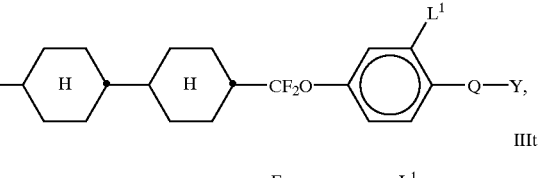
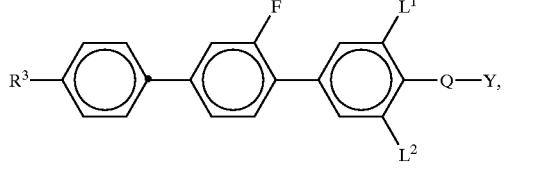
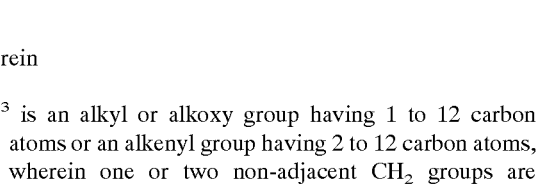
wherein
$R^3$ is an alkyl or alkoxy group having 1 to 12 carbon atoms or an alkenyl group having 2 to 12 carbon atoms, wherein one or two non-adjacent $CH_2$ groups are optionally replaced by —O—, —CH=CH—, —CO—, —OCO— or —CO—O— in a manner that O atoms are not linked directly to one another, and $L_1$ and $L_2$ are each, independently of one another, H or F.

7. A liquid-crystal mixture according to claim 1, comprising 5 to 30% by weight of one or more compounds of formula IA.

8. A liquid-crystal mixture according to claim 1, comprising 10 to 40% by weight of one or more compounds of formula IB.

9. A liquid-crystal mixture according to claim 1, comprising 25 to 60% by weight of one or more compounds of formula IC.

10. A TN, STN or IPS display comprising a liquid-crystal mixture according to claim 1.

11. A liquid-crystal mixture according to claim 1, wherein $R^a$ and $R^b$ are, each independently, a straight chain alkyl group having 1 to 8 carbon atoms or an alkenyl group having 2 to 8 carbon atoms, and wherein $R^c$ is an alkenyl having 2 to 7 carbon atoms.

12. A liquid-crystal mixture according to claim 1, comprising one or more compounds of formulae IA-1 to IA-4, IB-1 to IB-2, and IC-2 to IC-3,

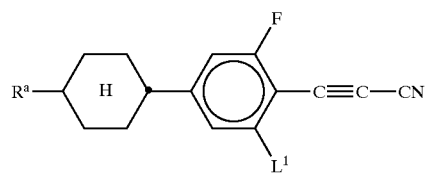

IA-1

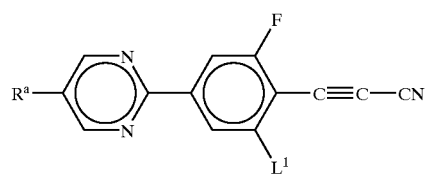

IA-2

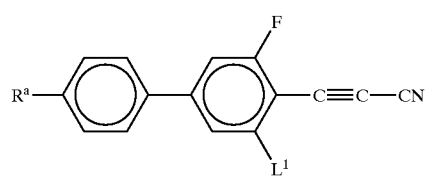

IA-3

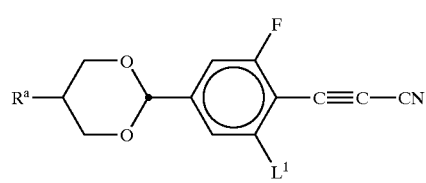

IA-4

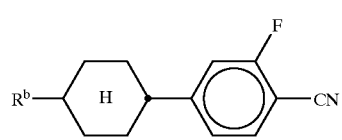

IB-1

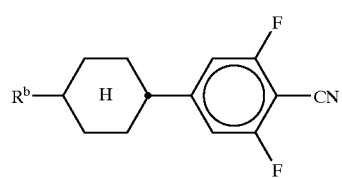

IB-2

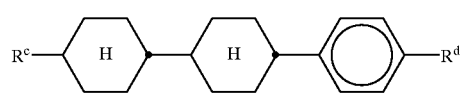

IC-2

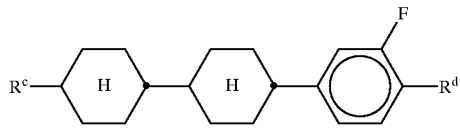

IC-3 wherein $R^a$, $R^b$, $R^c$ and $R^d$ are as defined in claim 1.

13. A liquid-crystal mixture according to claim 1, comprising one or more compounds of formulae IA-1a, IA-1b, IA-1c, IA-2a, IA-2b, IA-2c, IC-1a, IC-1b, IC-1c, IC-1d, IC-1e, IC-2a, IC-2b, IC-2c, IC-2d, IC-3a,

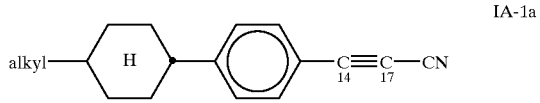

IA-1a

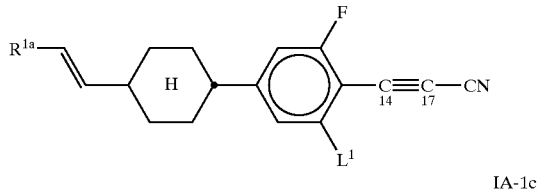

IA-1b

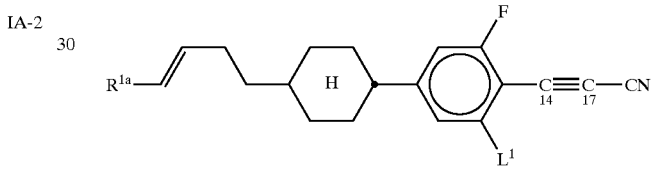

IA-1c

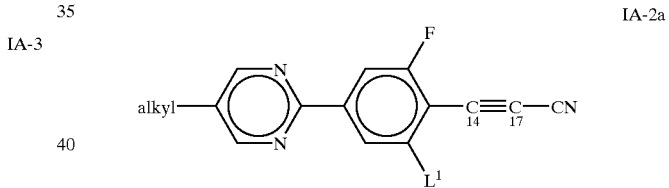

IA-2a

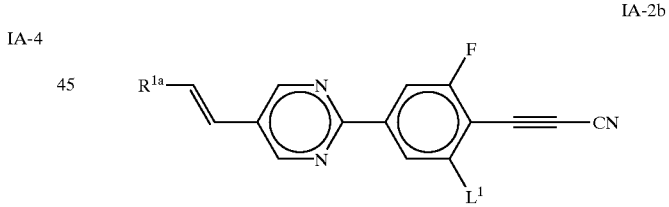

IA-2b

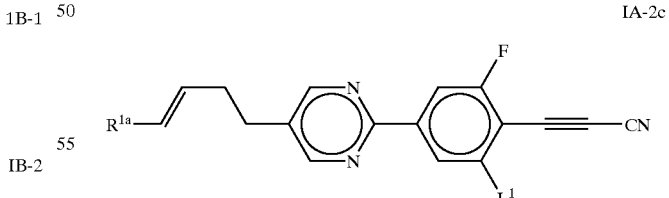

IA-2c

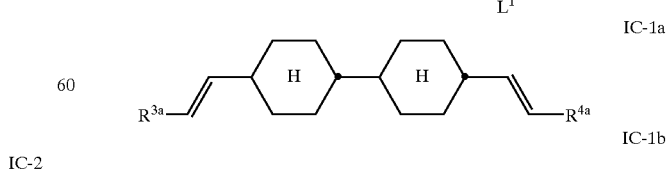

IC-1a

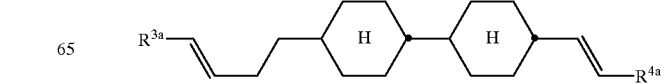

IC-1b

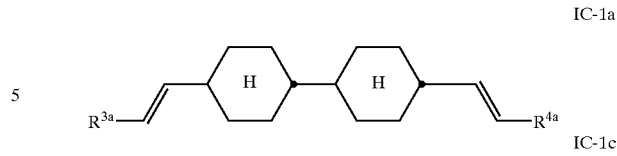

wherein $R^{3a}$, $R^{4a}$ are the same and selected from the group consisting of H, $CH_3$, $C_2H_5$ and n—$C_3H_7$.

17. A liquid-crystal mixture according to claim 12, wherein $R^d$ is F, $OCF_3$ or alkyl having 1 to 8 carbon atoms and $R^e$ is 1E-alkenyl or 3E-alkenyl having 2 to 7 carbon atoms in compounds of formulae IC-2 and IC-3.

18. A liquid-crystal mixture according to claim 3, wherein

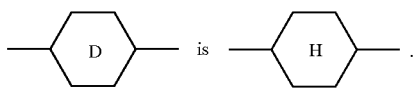

19. A liquid-crystal mixture according to claim 3, wherein $R^3$ is an alkyl or alkoxy having 1 to 8 carbon atoms, and Q—Y is F, Cl, $OCF_3$ or $OCHF_2$.

20. A liquid-crystal mixture according to claim 2, wherein $R^2$ is an alkyl or alkoxy having 1 to 8 carbon atoms.

21. A TN or STN liquid-crystal display according to claim 4, wherein the liquid crystal mixture comprises 20 to 70% by weight of a liquid-crystalline component A, 30 to 75% by weight of a liquid-crystalline component B, 0 to 10% of a component C, and no component D.

22. A TN or STN liquid-crystal display according to claim 4, wherein component A contains one or more compounds having a dielectric anisotrophy of greater than or equal to 3.

23. A TN or STN liquid-crystal display according to claim 4, wherein component A contains one or more compounds having a dielectric anisotrophy of greater than or equal to 12.

24. A liquid-crystal mixture according to claim 1, comprising 8 to 20% by weight of one or more compounds of formula IA, 10 to 30% by weight of one or more compounds of formula IB, and 25 to 50% by weight of one or more compounds of formula IC.

25. A liquid-crystal mixture according to claim 1, wherein more than 20% of the compounds have a positive dielectric anisotropy.

26. A liquid-crystal mixture according to claim 1, wherein more than 20% of the compounds have a positive dielectric anisotropy of greater than or equal to 12.

27. A TN or STN display according to claim 4, wherein component C is present in an amount whereby the ratio between the layer thicknesses and the natural pitch of the chiral nematic liquid-crystal mixture is 0.2 to 1.3.

28. A liquid-crystal mixture according to claim 1, further comprising one or more compounds of formula IB,

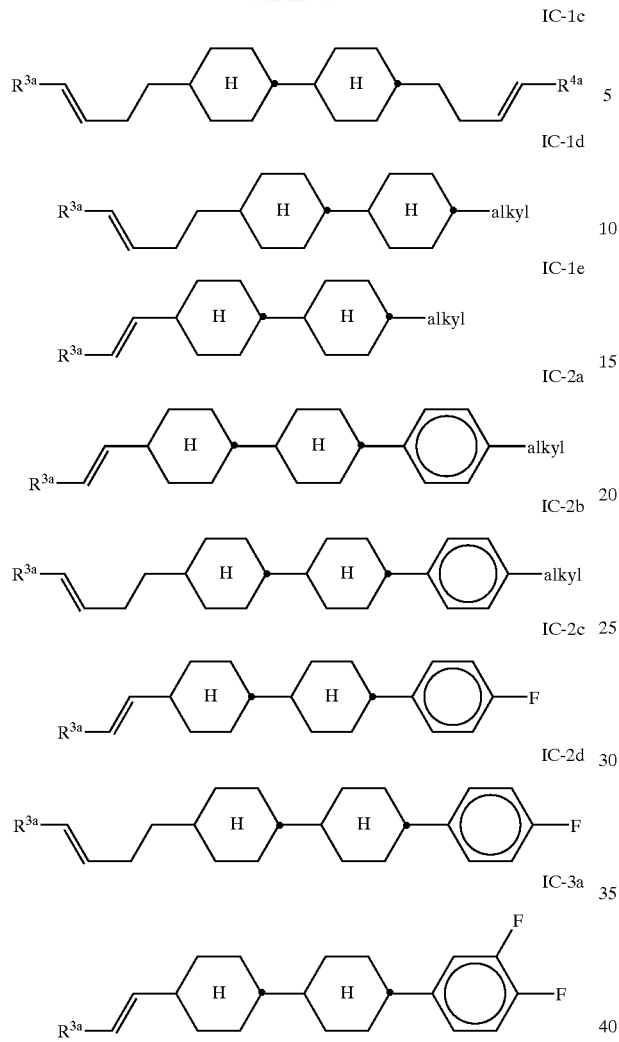

wherein $R^{1a}$, $R^{3a}$, $R^{4a}$ are, each independently, H, $CH_3$, $C_2H_5$ or n—$C_3H_7$, and alkyl is an alkyl group having 1 to 8 carbon atoms.

14. A liquid-crystal mixture according to claim 13, comprising one or more compounds of formulae IA-1a and IA-2a.

15. A liquid-crystal mixture according to claim 13, wherein $R^{1a}$ is H in IA-1b, IA-1c, IA2b and IS-2c, and $R^{3a}$ and $R^{4a}$ are $CH_3$ in IC-1a, and $R^{3a}$ is H in IC-1e.

16. A TN, STN or IPS display according to claim 4 comprising a compound of IC-1e

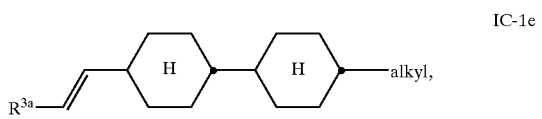

wherein $R^{3a}$ is H, $CH_3$, $C_2H_5$ or n—$C_3H_7$, and alkyl is an alkyl group having 1 to 8 carbon atoms, or a TN or STN display according to claim 4 comprising a compound of IC-1a and/or IC-1c

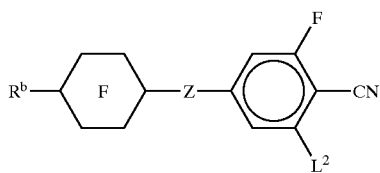

wherein

Z is —CO—O—, and $R^b$, $L^2$ and

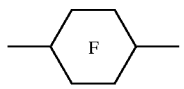

are as defined in claim 1.

29. A TN or STN liquid-crystal display according to claim 4, wherein the liquid-crystal mixture further comprises one or more compounds of formula IB,

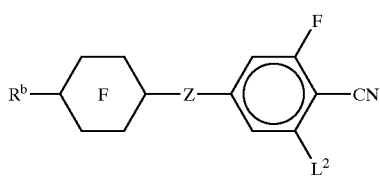

wherein

Z is —CO—O—, and $R^b$, $L^2$ and

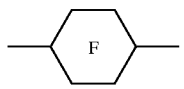

are as defined in claim 4.

30. A liquid-crystal mixture according to claim 28, comprising one or more compounds of formulae IB-3 to IB-7

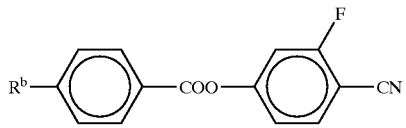

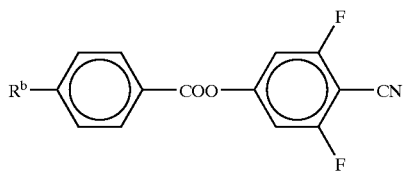

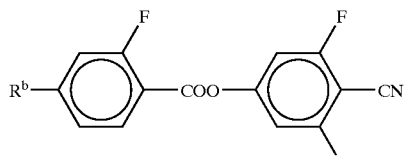

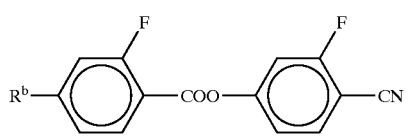

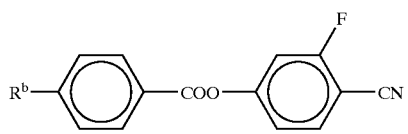

wherein $R^b$ is as defined in claim 28.

31. A TN or STN liquid-crystal display according to claim 29, comprising one or more compounds of formulae IB-3 to IB-7

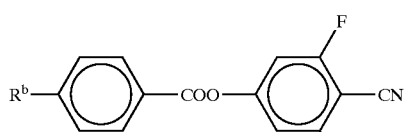

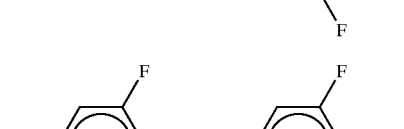

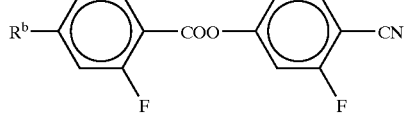

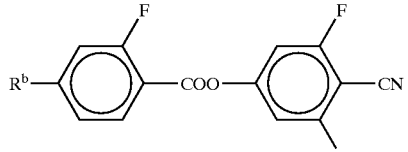

wherein $R^b$ is as defined in claim 28.

32. A liquid-crystal mixture according to claim 28, comprising one or more compounds of formulae IB-4a to Ib-4c

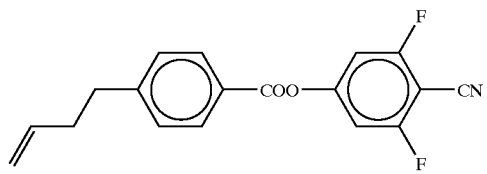

-continued
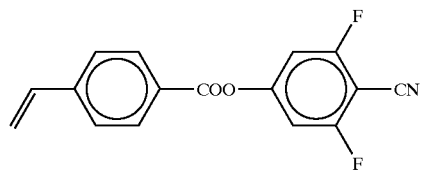
IB-4b
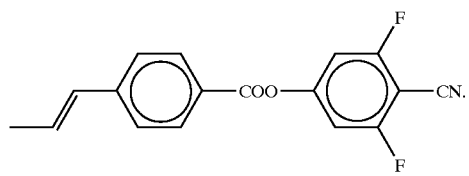
IB-4c
33. A TN or STN liquid-crystal display according to claim 29, comprising one or more compounds of formulae IB-4a to IB-4c
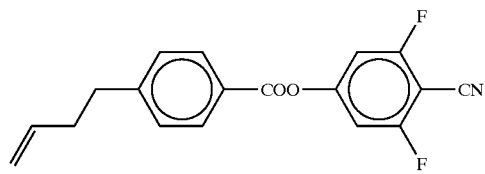
IB-4a
-continued
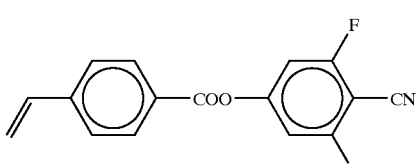
IB-4b
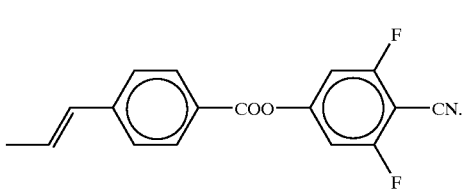
IB-4c
* * * * *

UNITED STATES PATENT AND TRADEMARK OFFICE
CERTIFICATE OF CORRECTION

PATENT NO.    : 6,821,582 B2
DATED         : November 23, 2004
INVENTOR(S)   : Hirschmann et al.

It is certified that error appears in the above-identified patent and that said Letters Patent is hereby corrected as shown below:

Column 47,
Line 54, "claim 4" should be -- claim 10 --.

Signed and Sealed this

Twenty-sixth Day of April, 2005

JON W. DUDAS
*Director of the United States Patent and Trademark Office*